United States Patent
Xu et al.

(10) Patent No.: US 10,189,862 B2
(45) Date of Patent: Jan. 29, 2019

(54) PHENOTHIAZINE-PYRIDINE COMPOUNDS AND USES THEREOF

(71) Applicant: The Chinese University of Hong Kong, Shatin (CN)

(72) Inventors: Chuanshan Xu, Shatin (CN); Qicai Xiao, Shatin (CN); Wing Nang Leung, Shatin (CN); Pan Wang, Shatin (CN); Hungkay Lee, Shatin (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/589,610

(22) Filed: May 8, 2017

(65) Prior Publication Data

US 2018/0002348 A1 Jan. 4, 2018

Related U.S. Application Data

(60) Provisional application No. 62/350,025, filed on Jun. 14, 2016.

(51) Int. Cl.
*C07D 513/04* (2006.01)
(52) U.S. Cl.
CPC .................. *C07D 513/04* (2013.01)
(58) Field of Classification Search
CPC .................................................. C07D 513/04
See application file for complete search history.

(56) References Cited

U.S. PATENT DOCUMENTS 7,371,744 B2  5/2008  Brown et al.

OTHER PUBLICATIONS

Pinedo et al. (2000).*
McMahon et al. (2000).*
Cieplik, et al., "Antimicrobial Photodynamic Therapy for Inactivation of Biofilms Formed by Oral Key Pathogens," Frontiers in Microbiology, vol. 5, Aug. 12, 2014, 17 pages.
Kharkwal, et al., "Photodynamic Therapy for Infections: Clinical Applications," Lasers in Surgery and medicine, 43:755-767 (2011).
Mellish et al., "In Vitro Photodynamic Activity of a Series of Methylene Blue Analogues," Photopchemistry and Photobiology, 2002, 75(4), 392-397.
Rice, et al., "Phenothiazine Photosensitizers. III. Activity of Methylene Blue Derivatives against Pigmented Melanoma Cell Lines," Journal of Chemotherapy, 12:1, 94-104.
Sperandio et al., "Antimicrobial Photodynamic Therapy to Kill Gram-Negative Bacteria,"Recent Pat Antiinfect Drug Discov. Aug. 2013; 8(2): 108-120.
Wainwright et al., "Photobactericidal activity of phenothiazinium dyes against methicillin-resistant strains of *Staphylococcus aureus*," FEMS Microbiology Letters 160 (1998) 177-181.

* cited by examiner

*Primary Examiner* — Paul V Ward
(74) *Attorney, Agent, or Firm* — Kilpatrick Townsend & Stockton LLP

(57) ABSTRACT

The present invention provides a novel phenothiazine-pyridine compound that is an effective photosensitizer useful for photodynamic therapy. Also provided is a method for inhibiting cell proliferation or for treating a disease involving inappropriate cell proliferation.

30 Claims, 7 Drawing Sheets

PHENOTHIAZINE-PYRIDINE COMPOUNDS AND USES THEREOF

RELATED APPLICATIONS

This application claims priority to U.S. Provisional Patent Application No. 62/350,025, filed Jun. 14, 2016, the contents of which are hereby incorporated by reference in the entirety for all purposes.

BACKGROUND OF THE INVENTION

Malignant tumors are a fatal disease threatening human beings. The global cancer reports published by the world health organization (WHO) in 2014 indicated that cancer patients are increasing rapidly. It is estimated that the morbidity will achieve 24 million cases by 2035. Moreover, almost half of the new cancer cases have occurred in Asia and most in China. While surgery, radiotherapy, chemotherapy and immunotherapy are the traditional modalities for treating cancer, these approaches have some limitations including side effects, poor response, so there is an urgent need to find novel alternative treatments. Photodynamic therapy (PDT) is an emerging therapeutic modality and has been approved in clinical application in the treatment of neoplastic diseases. The therapeutic process of PDT involves the following aspects: (1) The photosensitive drug (photosensitizer) is administered to the subject orally or intravenously, and the photosensitizer will preferentially accumulate in the pathological tissues due to the metabolizing difference between the normal tissues and pathogenic tissues; (2) Employing a light with a specific wavelength to illuminate the target tissue to activate the photosensitizer; (3) The activated photosensitizer will transfer the energy to the surrounding molecules to generate cytotoxic radicals or radical ions (Type I mechanism); or the activated photosensitizer will transfer the energy to molecular oxygen, to generate singlet oxygen (Type II mechanism). Both pathways directly or indirectly result in the cell destruction or death, while the individual light or photosensitizer has little effect.

Compared with traditional treatments, PDT has many advantages such as safety, targeting ability, minimally invasive, and also rapid recovery. PDT can not only kill the tumor cells directly, but also initiates the antitumor immune system, and thus prevents tumor recurrence and metastasis. The unique characteristics of selectively attacking and killing tumor cells while having minimal or even no damage to the surrounding normal tissues, make PDT a promising treatment.

Additionally, based on the intrinsic fluorescence and selectively localizing ability of the photosensitizer, photosensitizer can also be used for medical diagnosis, known as photodynamic diagnosis (PDD). With the development of novel light sources, optical fiber and other related technologies, the indications for PDT have expanded from the superficial tumors to deep tissue tumors. PDT can also be used to treat some benign diseases, such as microbial infections. During recent years, the globally occurrence of infectious diseases caused by microorganisms, especially antibiotic resistant pathogens are increasing, which has become a great threat to human health. Similar to tumor cells, pathogenic microorganisms have similar properties including fast propagation and metabolism, and thus there is an urgent need for novel treatments to solve the problem of drug resistance. The unique action mechanism, prominent advantages and repeatability make PDT a promising alternative to treating infectious diseases.

However, the key element in effective PDT treatment is the photosensitizer used. An ideal photosensitizer should have a high quantum yield (QY)-including singlet oxygen quantum yield (SOQY) and fluorescence quantum yield (FQY), strong absorption in the near infra-red region (600-900 nm), good selectivity, low dark toxicity, stable composition, well-defined structure, and easy preparation. Photofrin was the first photosensitizer approved by FDA, but it has many shortcomings, such as short wavelength absorption, complicated and unstable composition. The subsequently developed photosensitizers are mostly based on the tetrapyrole structure, such as protoporphyrin IX (PpIX) and its prodrug Aminolevulinic acid (ALA) are approved in US and Europe, Temopofin is approved in Europe, Norway and Iceland, Sulphonated Aluminium Phtaalocyanine is approved in Russia, as well as some preclinically and clinically tested photosensitizers, such as Bacteriochlorins, Texafrins, Chlorin e6 and Purlytin. Although porphyrin-based photosensitizers have been developed rapidly, the structures of this class of compounds are relatively complicated, preparation and purification are difficult, industrious production is of high cost, and have relatively strong skin photosensitivity.

Phenothiazines are a type of nonpoyphyrin-based compounds with a unique structure and simple preparation. This type of compounds also have a stable composition, high quantum yield, weak dark toxicity, good tumor selectivity, long and strong wavelength absorption, and can act both in type I and type II photochemical pathways. Most of these compounds are positively charged and have good water solubility, which help reduce or avoid the possibility of aggregation in aqueous solution. In addition, although most of the photosensitizers are effective to Gram-positive bacteria in photodynamic antimicrobial trials, they usually demonstrate poor effects or even non-effective to Gram-negative bacteria. Phenothiazine compounds are effective against both Gram-positive and -negative bacteria because of their intrinsically cationic properties which can readily bind to the negative charged membrane through electronic interaction. For instance, methylene blue (MB)-a typical analog of phenothiazine compounds, has been used to photo-disinfect blood products, sterilize dental cavities, and kill micro-organisms, including human immunodeficiency virus (HIV), hepatits B and C. However, methylene blue also has limitations, such as low stability. Recently, Wainwright et al. successively reported the photodynamic effects of a series of MB analogs, new methylene blue (NMB) and dimethyl methylene blue showed better photoactivities against tumor cells and microorganisms than MB (1998, 2012). Hereafter, Stanley B. Brown reported series of symmetric and unsymmetric MB analogs, and a derivative named PPA904 with n-butyl side chain showed better photoactivity than MB, and it was also effective in photodynamical inactivation of Gram-positive and Gram-negative bacteria (2002, 2008). Clinical II trials using PPA904 for PDT treating chronic leg ulcers were completed, and it showed excellent therapeutic effect. Therefore, there is a need for novel potent non-porphyrin-based photosensitizers with excellent physiochemical and photodynamic properties. The phenothiazines of this invention, which have been shown to be surprisingly effective photosensitizers, fulfill this and other related needs.

BRIEF SUMMARY OF THE INVENTION

In a first aspect, the present invention provides a phenothiazine-pyridine compound of formula (I):

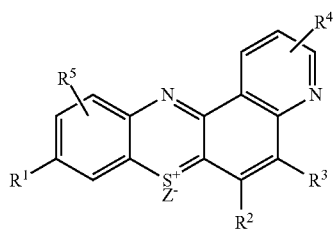

(I)

wherein: $R^1$ and $R^3$ are each

$R^2$ is H or halogen; $R^4$ is H, halogen, —NH$_2$, —OH, —CN, —NO$_2$, —COCH$_3$, —CF$_3$, $C_1$-$C_{10}$ alkyl, $C_1$-$C_{10}$ alkoxy, $C_1$-$C_{10}$ haloalkyl, $C_3$-$C_6$ cycloalkyl,

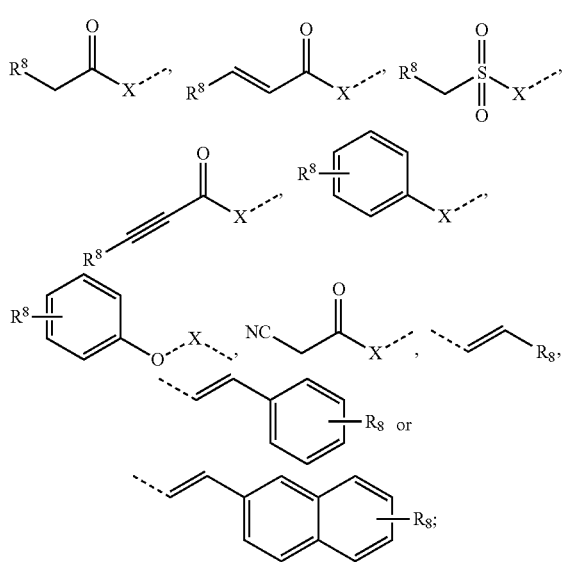

$R^5$ is H, halogen, —CN, —NO$_2$, —COCH$_3$, —CF$_3$, $C_1$-$C_{12}$ alkyl, $C_1$-$C_{12}$ alkoxy, $C_1$-$C_6$ alkoxycarbonyl, $C_3$-$C_6$ cycloalkyl or $C_2$-$C_{10}$ N-alkyl amine; $R^6$ and $R^7$ are each independently H, $C_1$-$C_{12}$ alkyl, $C_3$-$C_6$ cycloalkyl, $C_3$-$C_{12}$ alkenyl, $C_3$-$C_{12}$ alkynyl, $C_2$-$C_{10}$ amine or $C_2$-$C_{10}$ substituted amine, aryl, $C_nH_{2n}Y$, $YC_nH_{2n}Y$, or when taken together, $R^6$ and $R^7$ with a nitrogen to which they are both attached form a 5 to 7 membered heterocyclic ring wherein any one carbon atom of said heterocyclic ring can optionally be replaced with —O—, —S—, —SO$_2$— or —NR$^9$—; each $R^8$ is independently H, halogen, —NO$_2$, —CN, —COCH$_3$, —CF$_3$, $C_1$-$C_6$ alkyl, $C_1$-$C_6$ alkoxy, $C_3$-$C_6$ cycloalkyl or aryl; each $R^9$ is independently H, $C_1$-$C_{10}$ alkyl, $C_2$-$C_9$ carbonyl or $C_2$-$C_9$ sulfonyl; each n is independently an integer from 2 to 6; each X is independently selected from $C_1$-$C_5$ alkyl, O, S, NH$_2$, NH or NR$^{10}$; each Y is independently F, Cl, Br, I, OH, OMe, OC$_2$H$_5$, OC$_3$H$_7$, CN or OCOCH$_3$; each $R^{10}$ is independently $C_1$-$C_6$ alkyl, $C_1$-$C_6$ alkoxy, —NO$_2$, —CN, —COCH$_3$ or aryl; $Z^-$ is an organic or inorganic counter anion; or salts thereof.

In some embodiments, $R^4$ is H, $C_1$-$C_{12}$ alkyl, $C_1$-$C_{10}$ alkyl, $C_1$-$C_{10}$ alkoxy or $C_3$-$C_6$ cycloalkyl. In some embodiments, $R^4$ is H, —CH$_3$, —C$_2$H$_5$, —C$_3$H$_7$, —OCH$_3$, —OC$_2$H$_5$, —OC$_4$H$_9$, -cyclopropyl, -cyclobutyl, -cyclopentyl or -cyclohexyl. In some embodiments, $R^6$ and $R^7$ are each independently H, methyl, ethyl, propyl, n-butyl, n-pentyl, n-hexyl, n-heptyl, n-octyl, cyclopropyl, cyclobutyl, cyclopentyl, cyclohexyl, —CH$_2$(CH$_2$)$_2$NH$_2$, —CH$_2$(CH$_2$)$_3$NH$_2$, —CH$_2$(CH$_2$)$_4$NH$_2$, —CH$_2$(CH$_2$)$_5$NH$_2$, —N(CH$_3$)(CH$_2$)$_2$NH$_2$, N(CH$_3$)(CH$_2$)$_3$NH$_2$, N(CH$_3$)(CH$_2$)$_4$NH$_2$ or N(CH$_3$)(CH$_2$)$_5$NH$_2$. In some embodiments, when taken together, $R^6$ and $R^7$ with a nitrogen to which they are both attached form a 5 to 7 membered heterocyclic ring wherein any one carbon atom of said heterocyclic ring can optionally be replaced with —O—, —S—, —SO$_2$— or —NR$^9$—. In some embodiments, $R^6$ and $R^7$ are

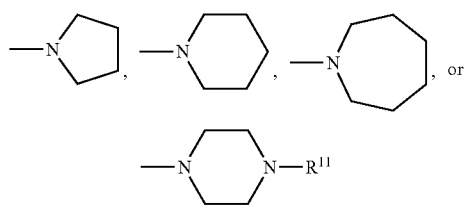

wherein $R^{11}$ is H, $C_1$-$C_{10}$ alkyl, $C_2$-$C_9$ carbonyl, or $C_2$-$C_9$ sulfonyl. In some embodiments, $R^6$ and $R^7$ are each independently H or $C_1$-$C_{12}$ alkyl. In some embodiments, $R^6$ and $R^7$ form a six membered azaoxa-ring or azathia-ring. In some embodiments, $R^6$ and $R^7$ form

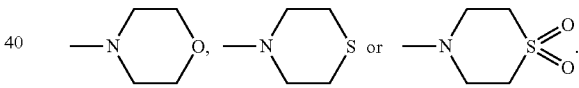

In some embodiments, $Z^-$ is a halide ion, NO$_2$—, CH$_3$CO$_2$—, NO$_2^-$, CH$_3$CO$_2^-$, CF$_3$CO$_2^-$, ClO$_4^-$, HSO$_4^-$, H$_2$PO$_4^-$, SCN$^-$, F$_4$B$^-$, lactate, citrate, tartrate, malate, glycolate, glycerate, gluconate, glutamate, or aspartate. In some embodiments, $Z^-$ is F$^-$, Cl$^-$, Br$^-$, I$^-$, CH$_3$COO$^-$, CF$_3$COO$^-$ or HSO$_4^-$.

In a second aspect, the phenothiazine-pyridine has the structure of Formula II:

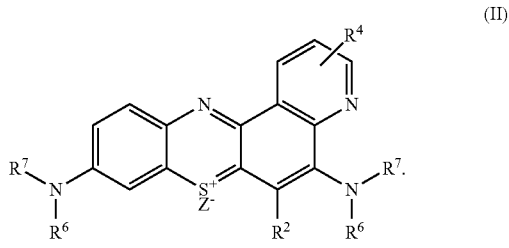

(II)

In a third aspect, the phenothiazine-pyridine has the structure of Formula III:

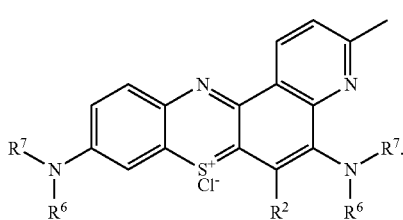

(III)

In a fourth aspect, the phenothiazine-pyridine compound is 5-amino-9-(diethylamino)-3-methylpyrido[3,2-a]phenothiazin-7-ium chloride, 9-(diethylamino)-3-methyl-5-(propylamino)pyrido[3,2-a]phenothiazin-7-ium chloride, 9-(diethylamino)-3-methyl-5-(pentylamino)pyrido[3,2-a]phenothiazin-7-ium chloride, 9-(diethylamino)-5-(heptylamino)-3-methylpyrido[3,2-a]phenothiazin-7-ium chloride, 5-(decylamino)-9-(diethylamino)-3-methylpyrido[3,2-a]phenothiazin-7-ium chloride, 9-(diethylamino)-3-methyl-5-(methylamino)pyrido[3,2-a]phenothiazin-7-ium chloride, 9-(diethylamino)-5-(dipropylamino)-3-methylpyrido[3,2-a]phenothiazin-7-ium chloride, 9-(diethylamino)-5-(dipentylamino)-3-methylpyrido[3,2-a]phenothiazin-7-ium chloride, 5-(3-aminopropylamino)-9-(diethylamino)-3-methylpyrido[3,2-a]phenothiazin-7-ium chloride, 9-(diethylamino)-3-methyl-5-(3-(methylamino)propylamino)pyrido[3,2-a]phenothiazin-7-ium chloride, 9-(diethylamino)-6-iodo-3-methyl-5-(propylamino)pyrido[3,2-a]phenothiazin-7-ium chloride or 9-(dibutylamino)-3-methyl-5-(propylamino)pyrido[3,2-a]phenothiazin-7-ium chloride.

Aside from their chemical structures described above, the phenothiazine-pyridine compounds of this invention are photosensitizers. In other words, they share the same or similar functional feature of being able to generate cytotoxic radicals or radical ions (Type I mechanism) or generate singlet oxygen (type II mechanism) upon receiving an excitation light (e.g., in the wavelength range of about 600-900 nm), so as to inhibit target cell proliferation by causing target cells death or damaging the target cells and rendering them unviable.

In a fifth aspect, the present invention provides a pharmaceutical composition including (1) a photosensitizer such as a compound that has the general structure of Formula I and is described above and herein; and (2) a pharmaceutically acceptable excipient.

In a sixth aspect, the present invention provides a method for inhibiting cell proliferation. The method includes the steps of (a) contacting a target cell, which is typically undergoing inappropriate proliferation, such as a malignant tumor cell or infectious bacterial cell, with an effective amount of a phenothiazine-pyridine compound described herein; and (b) exposing the compound, along with the target cell in its vicinity, to a light that has an appropriate wavelength of about 600-900 nm (for example, about 600-700 nm), the phenothiazine-pyridine compound then causes death of the target cell, either by cytotoxic radical/radical ions or by singlet oxygen generated by the light-activated phenothiazine-pyridine compound. In some embodiments, the target cell is a tumor cell or a cancer cell. In some embodiments, the target cell is a bacterial cell, which may be a Gram-positive or Gram-negative bacterium, such as *E. coli* or *S. aureus*. In some embodiments, the target cell is within the body of a subject, such as a human or animal subject.

Thus, the method described herein effectively provides a therapeutic method for treating a proliferative disease in a subject, including various types of cancer or infections involving microbial pathogens such as bacteria and viruses. Tumors/cancers that can be treated in this manner include lung cancer, pancreatic cancer, breast cancer, colorectal cancer, colon cancer, esophageal cancer, oral cancer, lymphoma, penis cancer, prostate cancer, skin cancer, gynecological cancer, gastrointestinal stromal tumor, head tumor, neck tumor, eye tumor, and the like. Bacterial infections that can be treated in this manner include infections caused by Gram-positive bacteria and Gram-negative bacteria, such as *E. coli* or *S. aureus*. In some embodiments, the method described herein effectively provides a therapeutic method for treating ophthalmic diseases (AMD), arthritis, atherosclerosis, and restenosis. Various routes of administration may be employed for delivering the compound to a subject, including oral ingestion, topical application, and injection (such as subcutaneous, intravenous, intramuscular, intraperitoneal, and intratumoral injection).

In a seventh aspect, the present invention provides a composition in which the phenothiazine-pyridine compound described herein is present with a proliferating cell or a multitude of proliferating cells, such as malignant proliferating cells (e.g., tumor or cancer cells) or benign proliferating cells (e.g., bacterial cells, which may be Gram-positive or Gram-negative bacterial cells, such as *E. coli* or *S. aureus*). In some embodiments, the present invention provides a composition in which the phenothiazine-pyridine compound described herein is present with benign proliferative diseases including but are not limited to port wine stains (PWS), lupus, and acne or virus infections, including but are not limited to HIV, genital warts, and hepatits B and C, or parasite infection, including but are not limited to *Leishmania* protozoan and *Plasmodium* spp. The composition in some cases may be present while exposed to or immersed in a light of about 600-900 nm wavelength.

In an eighth aspect, the present invention provides a composition in which the phenothiazine-pyridine compound described herein can be used as diagnostic agents for their intrinsic fluorescent properties and ability to readily to concentrate in tumor and diseased tissue.

In a related aspect, the present invention provides use of a phenothiazine-pyridine compound described herein for manufacturing a medicament for treating a disease or disorder in which inappropriate or undesirable cell proliferation is present, such as cancer or microbe infection (e.g., bacterial infection). The phenothiazine-pyridine compound, which exhibits a photodynamic activity, can be formulated with one or more physiologically acceptable excipients for administration to a subject who has been diagnosed with the disease or disorder. The phenothiazine-pyridine compound may be formulated for administration via various routes, such as oral ingestion, topical application, or injection including subcutaneous, intravenous, intramuscular, intraperitoneal, and intratumoral injection.

In addition, the present invention provides a composition or method that utilizes the phenothiazine-pyridine compound described herein for inactivation and sterilization of various objects (such as textiles, leather, operation table, package materials), biomedical materials (such as artificial organs, medical catheter and tissue repair materials), fluids (such as water, blood samples) as well as foods, beverages, and household supplies.

DEFINITIONS

Figure 1:
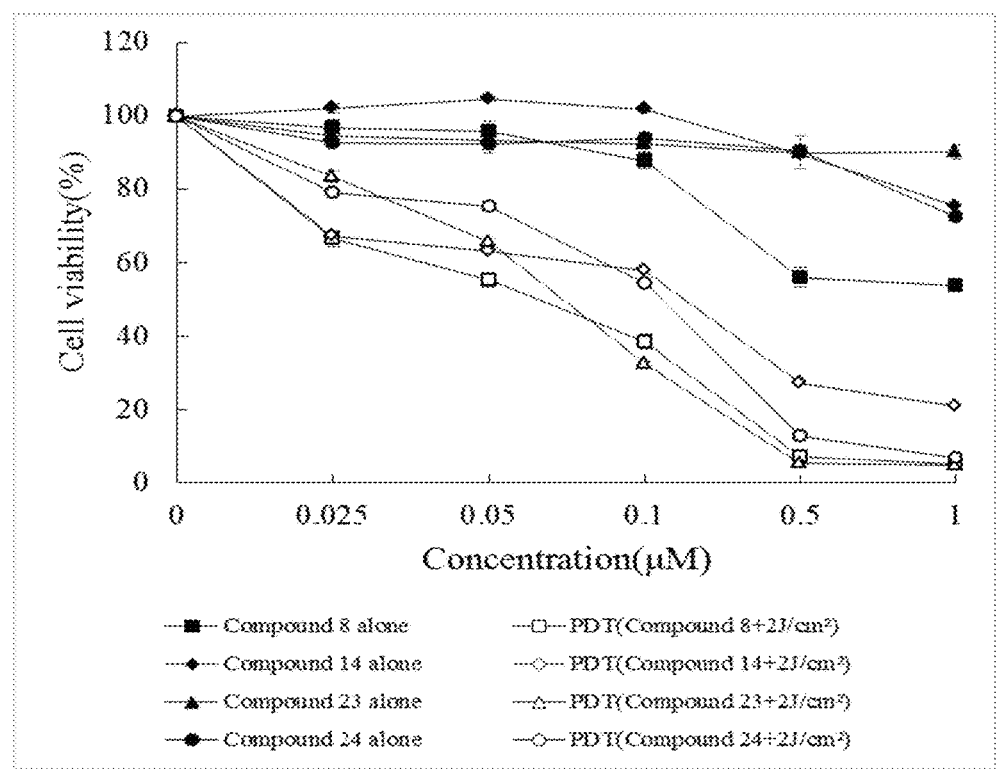
FIG. 1 shows the cytotoxic effects of compound 8, 14, 23, and 24 to MDA-MB-231 cells in the absence (closed symbols) and presence (open symbols) of light (635 nm Laser).

As used herein, the term "halogen" refers to fluorine, chlorine, bromine and iodine.

The term "alkyl" as used herein refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "alkoxy" as used herein refers to an alkyl group, as defined above, having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

The term "haloalkyl" as used herein refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

The term "cycloalkyl" as used herein refers to a saturated or partially unsaturated, monocyclic, fused bicyclic or bridged polycyclic ring assembly containing from 3 to 12 ring atoms, or the number of atoms indicated monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$ cycloalkyl includes cyclopropyl, cyclobutyl, cyclopentyl, cyclohexyl, cyclooctyl, and norbornane.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "amine" as used herein refers to an alkyl groups as defined within, having one or more amino groups. The amino groups can be primary, secondary or tertiary. The alkyl amine can be further substituted with a hydroxy group. Amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

As used herein, the term "alkenyl" refers to either a straight chain or branched hydrocarbon having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

As used herein, the term "alkynyl" refers to either a straight chain or branched hydrocarbon having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

The term "aryl" as used herein refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

As used herein, the term "heterocyclic ring" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, "carbonyl" means a functional group composed of a carbon atom double-bonded to an oxygen atom: C=O. Carbonyls include without limitation, aldehydes, ketones, carboxylic acids, esters, and amides.

The term "sulfonyl," as used herein, alone or in combination, refers to —SO$_2$—.

Unless specially mentioned the alkyl, alkoxy, haloalkyl cycloalkyl, alkoxycarbonyl, amine, alkenyl, alkynyl, aryl, heterocyclic ring, carbonyl, and sulfonyl of the present invention can be substituted or unsubstituted. For example, $C_1$-$C_6$ alkyl group can be substituted by one, two, or three substitutes selected from hydroxyl, halogens, alkoxyl, dialkylamino, or heterocyclic ring such as morpholinyl, piperidinyl groups.

As used herein, "counter anion" or "anion," refers to a negatively charged ion. Examples of counter anions include, but are not limited to a halide ion, $NO_2$—, $CH_3CO_2$—, $NO_2^-$, $CH_3CO_2^-$, $CF_3CO_2^-$, $ClO_4^-$, $HSO_4^-$, $H_2PO_4^-$, $SCN^-$, $F_4B^-$, lactate, citrate, tartrate, malate, glycolate, glycerate, gluconate, glutamate, and aspartate.

As used in this application, an "increase" or a "decrease" refers to a detectable positive or negative change in quantity from a comparison control, e.g., an established standard control (such as an average cellular proliferation rate or cell death rate found in untreated target cells of the same type). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "inhibiting" or "inhibition," as used herein, refers to any detectable negative effect on a target biological process, such as cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., cell death rate or proliferation rate among target cells) upon application of an inhibitor, when compared to a control where the inhibitor is not applied.

The term "about," when used in the context of referring to a pre-determined value, describes a range of value that is +/−10% from the pre-determined value.

The term "treat" or "treating," as used in this application, describes an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount," as used herein, refers to an amount of a given substance that is sufficient in quantity to produce a desired effect. For example, an effective amount of a photosensitizer is the amount of said compound to achieve a decreased level of target cell proliferation rate or increased target cell death rate, such that the symptoms, severity, and/or recurrence change of a disease or condition involving improper proliferation of such target cells are reduced, reversed, eliminated, prevented, or delayed of the onset in a subject who has been given the compound for therapeutic purposes. An amount adequate to accomplish this is defined as the "therapeutically effective dose." The dosing range varies with the nature of the therapeutic agent being administered and other factors such as the route of administration and the severity of a subject's condition.

The term "subject" or "subject in need of treatment," as used herein, includes humans or animals in need medical attention due to risk of, or actual suffering from, a disease or condition involving inappropriate or undesirable cell proliferation such as an infection or any type of cancer. Subjects also include individuals currently undergoing therapy that seek manipulation of the therapeutic regimen. Subjects or individuals in need of treatment include those that demonstrate symptoms of such disease or condition or are at risk of suffering from disease/condition or its symptoms. For example, a subject in need of treatment includes individuals with a genetic predisposition or family history for various types of cancer, those that have suffered relevant symptoms in the past, those that have been exposed to a triggering substance or event, as well as those suffering from chronic or acute symptoms of the condition. A "subject in need of treatment" may be at any age of life.

DETAILED DESCRIPTION OF THE INVENTION

I. Introduction

The present invention relates to phenothiazine-pyridine compounds, their pharmaceutically acceptable compositions, medical compositions, and use of these compounds and compositions in photodynamic therapy (PDT), as well as in diagnosis and detection and in photodisinfection or photosterilisatiom.

The key element in effective PDT treatment is the photosensitizer and the present invention describes the preparation and uses of a series of novel phenothiazine-pyridine-based photosensitizers. The compounds of the present invention have relatively simple structure, long wavelength absorption, high singlet oxygen generation, and good selectivity between tumor cells and normal cells. Compounds of the present invention can also kill many kinds of tumor cells under light activation. Furthermore, compounds of the present invention can quickly and efficiently eradicate various bacteria under light activation. The abundant of the starting material, easy preparation process, and promising photodynamic activities make these compounds possess significant value for uses.

II. Phenothiazine-Pyridine Compounds of This Invention

The present invention provides compounds that are activated by light, which has an appropriate wavelength, usually in the range of 600-900 nm, preferably 630-700 nm. The light sources may be any appropriate light sources, including but are not limited to laser (including pulse laser and continuous laser), diodes, hernia light, etc. The light dose is 1-200 J/cm², preferably is 1-100 J/cm². Light illumination can be given at any time of 0-24 h after a drug is administered, preferably is during 0-6 h, and more preferably is 10 min-3 h. It is preferred that exposure to light is localized to the pathological region, and the increased light intensity usually reduces the exposure time.

The present invention provides novel phenothiazine-pyridine compounds that can serve as excellent photsensitizers for use in photodynamic therapy (PDT) to treat proliferative diseases including benign proliferative diseases (such as those caused by microbe infection, e.g., bacterial or viral) and malignant proliferative diseases (such as various tumors and especially cancers).

III. Synthesis of the Phenothiazine-Pyridine Compounds

Apart from the methods that are known in the literature or exemplified in the experimental procedures in the standard methods, the compounds of formula I mentioned in this invention can be prepared as the following scheme. Therefore, the following scheme is just used for illustration. It is not limited to the listed compounds or any particular substituent. The number of substituents showed in this scheme is not required to match the number that used in the claim, and for the purpose of clarity. The compounds of formula I in this invention, can be prepared by people who skilled in this field in two steps by using analogs of aniline and quinoline. The preparation scheme is very simple, and the starting materials are all commercially available. It is easy for industrialization. Wherein, A, B, C, D, X and Z are selected as above, compound 1 and 3 can directly come from commercially available materials, or are prepared through the commercially available materials, such as compound 3a and 3b.

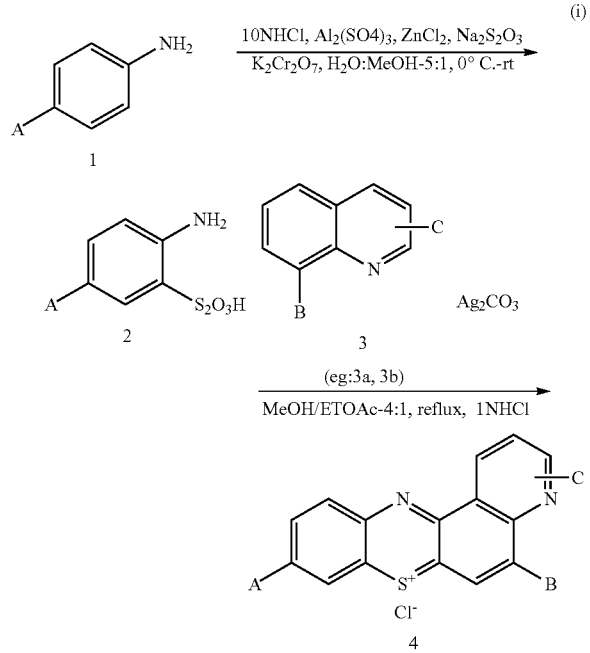

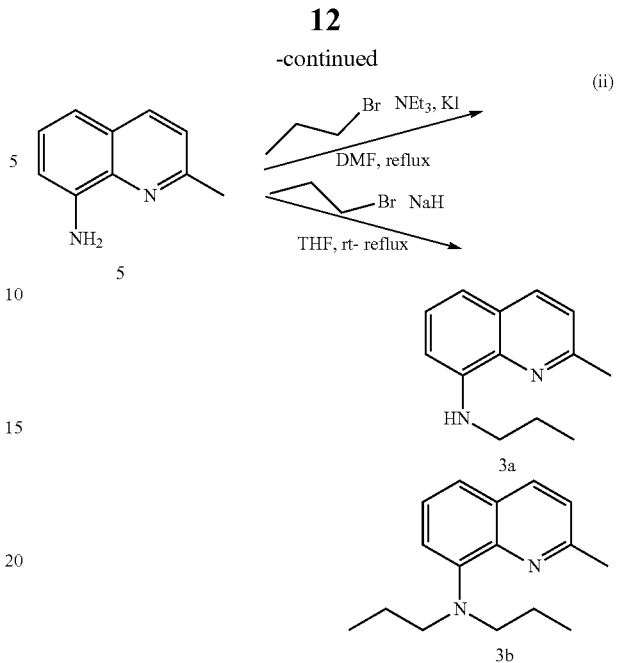

VI. Inhibition of Proliferating Cells and Treatment of Proliferative Diseases By demonstrating that the phenothiazine-pyridine compounds of this invention are effective photosensitizers capable of generating cytotoxic radicals/radical ions or generating singlet oxygen upon exposure to a light of the appropriate wavelength, e.g., between about 600 to 900 nm, preferably between 600 to 700 nm, the present inventors have established that these novel phenothiazine-pyridine compounds are useful for inhibiting cell proliferation by killing predetermined target cells, such proliferating cells including malignant cells (tumor cells) and bacterial cells. These compounds are therefore useful therapeutic agents for photodynamic therapy for diseases or conditions where improper proliferation is present. These diseases and conditions may involve malignant proliferation (e.g., various types of cancer) or benign proliferation (e.g., infection by microbes such as bacteria, viruses or parasites).

A. Pharmaceutical Compositions

Compounds of the present invention are useful in the manufacture of a pharmaceutical composition or a medicament. A pharmaceutical composition or medicament can be administered to a subject for the treatment of a proliferative disease.

The phenothiazine-pyridine compounds of the present invention are suitable in the manufacture of a pharmaceutical composition or a medicament comprising an effective amount thereof in conjunction or mixture with excipients or carriers suitable for application.

An exemplary pharmaceutical composition of this invention comprises (i) one or more phenothiazine-pyridine compounds as described herein, and (ii) a pharmaceutically acceptable excipient or carrier. The terms pharmaceutically-acceptable and physiologically-acceptable are used synonymously herein. The phenothiazine-pyridine compound(s) may be provided in a therapeutically effective dose for use in a method for treatment as described herein.

The pharmaceutical compositions of the carriers include but are not limited to: liposomes, nanoparticles, vesicles, microbubbles, microspheres, nano-bubbles, micelles, emulsions, gels, liquid crystals, biomedical materials, etc. The compositions can be composed of general delivery vehicles or accessories, including but not limited to ethyl alcohol, polyethylene glycol, dimethylsulfoxide, Tween, glycerol, castor oil, buffers, etc.

A phenothiazine-pyridine compound of this invention can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the compound to be delivered is incorporated as part of a liposome, alone or in conjunction with a molecule which binds to, e.g., a receptor prevalent among the targeted cells (e.g., epithelial cells), or with other therapeutic or immunogenic compositions. Thus, liposomes filled with a phenothiazine-pyridine compound of the invention can be directed to the site of treatment, where the liposomes then deliver the composition. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The phenothiazine-pyridine compounds of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

B. Routes of Administration

Suitable formulations for topical application, e.g., to the skin and eyes, are preferably aqueous solutions, ointments, creams or gels well-known in the art. These formulations may contain solubilizers, stabilizers, tonicity enhancing agents, buffers and/or preservatives.

Suitable formulations for transdermal application include an effective amount of a phenothiazine-pyridine compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a phenothiazine-pyridine compound, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the phenothiazine-pyridine compound of this invention.

The phenothiazine-pyridine compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a phenothiazine-pyridine compound of this invention, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The phenothiazine-pyridine compounds can also be formulated in rectal compositions, for example, suppositories or retention enemas, for example, containing conventional suppository bases, for example, cocoa butter or other glycerides.

Furthermore, the phenothiazine-pyridine compounds can be formulated as a depot preparation. Such long-acting formulations can be administered by implantation (for example, subcutaneously or intramuscularly) or by intramuscular injection. Thus, for example, the phenothiazine-pyridine compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a phenothiazine-pyridine compound as described herein that acts as an effective photosensitizer, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a phenothiazine-pyridine compound of the present invention).

Administration may be by the same or different route of administration or together in the same pharmaceutical formulation.

C. Dosage

Pharmaceutical compositions or medicaments can be administered to a subject at a therapeutically effective dose to prevent, treat, or control a proliferative disease as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each individual compound of the phenothiazine-pyridine compounds described herein may have a unique dosage. A unit dosage for oral administration to a mammal of about 50 to 70 kg may contain between about 5 and 500 mg of the compound. Typically, a dosage of the phenothiazine-pyridine compound of the present invention is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, the phenothiazine-pyridine compounds may be administered for multiple days at the therapeutically effective daily dose. Thus, therapeutically effective administration of the compounds to treat a pertinent condition or disease described herein in a subject requires periodic (e.g., daily) administration that continues for a period ranging from three days to two weeks or longer. Typically, the phenothiazine-pyridine compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the agents every other day, every third day, or, if higher dose ranges are employed and tolerated by the subject, once a week.

Optimum dosages, toxicity, and therapeutic efficacy of the compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Particular compounds that exhibit large therapeutic indices are preferred. While compounds that exhibit toxic side effects can be used, care should be taken to design a delivery system that targets such compounds to the site of affected tissue to minimize potential damage to normal cells and thereby reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Exemplary dosages for a phenothiazine-pyridine compound described herein are provided. Dosage for a phenothiazine-pyridine compound can be between 0.1-0.5 mg/eye, with intravitreous administration (e.g., 5-30 mg/kg). The compounds can be administered orally at between 5-1000 mg, or by intravenous infusion at between 10-500 mg/ml. In the alternative, the compounds can be administered by intravenous injection or infusion at 50-500 mg/ml (over 120 minutes); 1-500 mg/kg (over 60 minutes); or 1-100 mg/kg (bolus) five times weekly. The phenothiazine-pyridine compounds can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, antibiotics, and the like. The additional therapeutic compound can be administered at the same time as, or even in the same composition with, main active ingredient (e.g., a phenothiazine-pyridine compounds of this invention). The additional therapeutic compound can also be administered separately, in a separate composition, or a different dosage form from the main active ingredient. Some doses of the main ingredient, such as a novel phenothiazine-pyridine compound described herein, can be administered at the same time as the additional therapeutic compound, while others are administered separately, depending on the particular symptoms and characteristics of the individual.

The dosage of a pharmaceutical composition of the present invention can be adjusted throughout treatment, depending on severity of symptoms, frequency of recurrence, and physiological response to the therapeutic regimen. Those of skill in the art commonly engage in such adjustments in therapeutic regimen.

VII. Kits

In addition to pharmaceutical compositions, the invention provides kits for practicing the methods described herein for treating a proliferative disease in a subject. For example, the kits may contain a collection of separate containers, each containing a single dose of a pharmaceutical composition comprising a phenothiazine-pyridine compound of this invention suitable to act as a photosensitizer for a photodynamic therapy regimen for treating the proliferative disease, which may be a malignant tumor or an infection caused by a microbe such as a bacterium. Frequently, the kits further contain instructional material providing description for a user to administer the pharmaceutical composition comprising the phenothiazine-pyridine compound of this invention.

EXAMPLES

The following examples are provided by way of illustration only and not by way of limitation. Those of skill in the art will readily recognize a variety of non-critical parameters that could be changed or modified to yield essentially the same or similar results.

Example 1 Compound 7:
2-amino-5-(diethylamino)benzenesulfonoperoxothioic O-acid

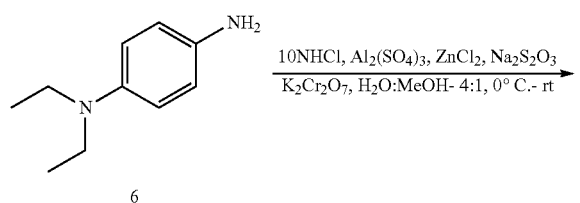

1.2 mL HCl (10 N,) was added to a solution of N,N-diethyl-p-phenylenediamine 6 (2.01 g, 12.0 mmol) in water and methanol (24 mL, H$_2$O/MeOH 4:1), the mixture was stirred at room temperature. A solution of aluminium sulfate (4.31 g, 12.6 mmol in 10 mL water), ZnCl$_2$ (1.72 g, 12.6 mmol in 2 mL water) were added to the above solution with stirring. The reaction mixture was cooled to 0° C., then an aqueous solution of new prepared sodium thiosulfate (3N, 8 mL) was added, after stirring for 5 min, a new prepared solution of potassium dichromate (0.5 N, 7.2 mL) was slowly added and stirred for 3 h at 0° C., then warmed up to room temperature and stirred for 1 h, a thick precipitate was obtained. The reaction mixture was filtered, and the gray solid were washed with water and acetone, dried under vacuum to afford a gray solid of 7 (2.39 g, 72%), which was used as such in the next steps.

Example 2 Compound 8: 5-amino-9-(diethylamino)-3-methylpyrido[3,2-a]phenothiazin-7-ium chloride

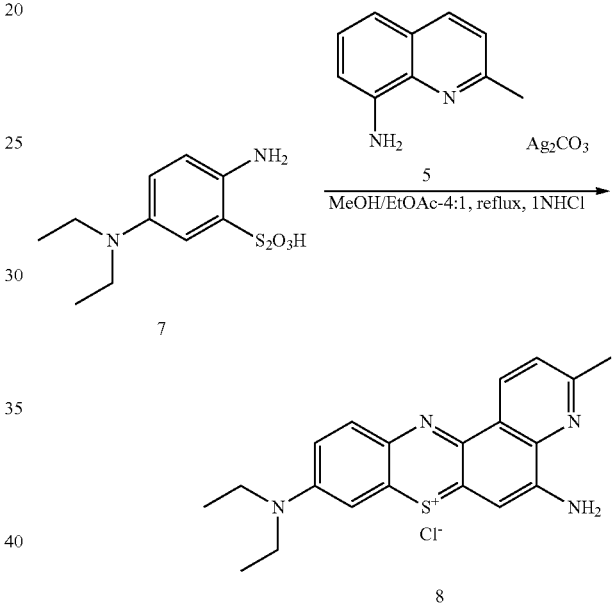

To a stirred and refluxed solution of compounds 7 (0.14 g, 0.5 mmol) and 5 (40.4 mg, 0.25 mmol) in methanol and ethyl acetate (6 mL, MeOH/Ethyl Acetate 4:1), was slowly added silver carbonate (0.14 g, 0.5 mmol), and the reaction mixture turned blue. After refluxing for 2 h, the reaction mixture was cooled to room temperature, filtered by celite, and the solid was washed by MeOH and dichloromethane. The organic layer was concentrated to afford a blue solid, which was redissolved in 5 mL dichloromethane and acidified with 0.25 mL HCl (1N in MeOH). The mixture was mixed gently, concentrated and purified by flash chromatography to afford a deep blue solid of 8 (31.1 mg, 32%). $^1$H NMR (400 MHz, MeOD): δ 9.01 (d, J=8.4 Hz, 1H), 7.91 (d, 9.6 Hz, 1H), 7.72 (d, J=8.5 Hz, 1H), 7.36 (dd, J=9.5, 2.8 Hz, 1H), 7.22 (d, J=2.8 Hz, 1H), 7.21 (s, 1H), 3.70 (q, J=7.1 Hz, 4H), 2.77 (s, 3H), 1.34 (t, J=7.1 Hz, 6H); $^{13}$C NMR (100 MHz, CDCl$_3$): δ 162.0 (C), 155.5 (C), 153.0 (C), 139.7 (C), 139.2 (C), 138.6 (CH), 134.2 (C), 134.1 (CH), 133.5 (C), 133.3 (C), 128.7 (C), 127.7 (CH), 119.2 (CH), 106.5 (CH), 106.4 (CH), 47.1 (CH$_2$), 24.9 (CH$_3$), 13.2 (CH$_3$) ppm. LCMS (ESI, relative intensity): m/z 349 ([M-Cl$^-$]$^+$, 100). UV-Vis (EtOH): λmax (nm) 658, log ε 4.93.

Example 3 Compound 3a: 2-methyl-N-propylquinolin-8-amine

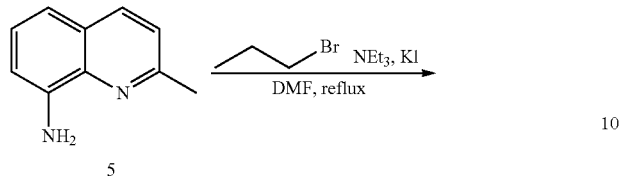

A stirred solution of 8-aminoquinaldine 5 (0.65 g, 4 mmol), 1-bromopropane (1.48 g, 12 mmol), triethylamine (3.5 mL), and KI (66.4 mg) in DMF (10 mL) was refluxed at 80° C. for 72 h, then cooled to room temperature, and added 20 mL water, the mixture was extracted by diethylether (10 mL×3), the combined organic phase was washed by saturated $NH_4Cl$ and NaCl, dried by $Na_2SO_4$. The residue was concentrated and purified by flash chromatography to afford a pale yellow oil of 3a (0.477 g, 60%). $^1H$ NMR (400 MHz, $CDCl_3$): δ 7.94 (d, J=8.4 Hz, 1H), 7.35-7.31 (m, 1H), 7.24 (d, J=8.4 Hz, 1H), 7.01 (d, J=8.1 Hz, 1H), 6.67 (d, J=7.6 Hz, 1H), 6.21 (br, 1H), 3.30 (q, J=6.6 Hz, 2H), 2.72 (s, 3H), 1.88-1.79 (m, 2H), 1.10 (t, J=7.4 Hz, 3H); $^{13}C$ NMR (100 MHz, $CDCl_3$): δ 155.6 (C), 144.6 (C), 137.6 (C), 136.2 (CH), 126.9 (CH), 126.7 (C), 122.1 (CH), 113.4 (CH), 104.6 (CH), 45.4 ($CH_2$), 25.3 ($CH_3$), 22.7 ($CH_2$), 12.0 ($CH_3$) ppm. LCMS (ESI, relative intensity): m/z 201 ([M+H]$^+$, 100).

Example 4 Compound 3b: 2-methyl-N,N-dipropylquinolin-8-amine

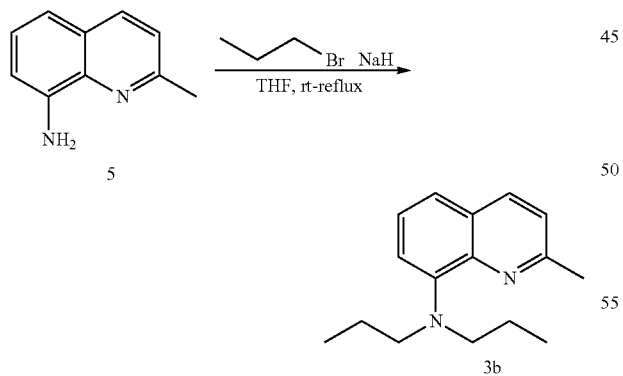

Compound of 8-aminoquinaldine 5 (0.24 g, 1.5 mmol) and 1-bromopropane (0.74 g, 6 mmol) were dissolved in anhydrous THF (10 mL). Sodium hydride (0.24 g, 6 mmol) was added in portions. The mixture was stirred at room temperature for 0.5 h, then heated to reflux for 36 h, after cooled to room temperature, saturated $NH_4Cl$ (3 mL) was added and stirred for 5 min. After removal of the THF under reduced pressure, the residue was extracted by diethylether (10 mL×3), the combined organic phase was washed by saturated $NH_4Cl$ and NaCl, dried by $Na_2SO_4$, concentrated and purified by flash chromatography to afford a pale yellow oil of 3b (0.14 g, 39%). $^1H$ NMR (400 MHz, $CDCl_3$): δ 7.94 (d, J=8.4 Hz, 1H), 7.33-7.29 (m, 1H), 7.24 (d, J=1.3 Hz, 1H), 7.20 (d, J=8.4 Hz, 1H), 7.02 (dd, J=7.5, 1.2 Hz, 1H), 3.46-3.42 (m, 4H), 2.72 (s, 3H), 1.70-1.65 (m, 4H), 0.89 (t, J=7.4 Hz, 6H) LCMS (ESI, relative intensity): m/z 243 ([M+H]$^+$, 100).

Example 5 Compound 10: tert-butyl 3-bromopropylcarbamate

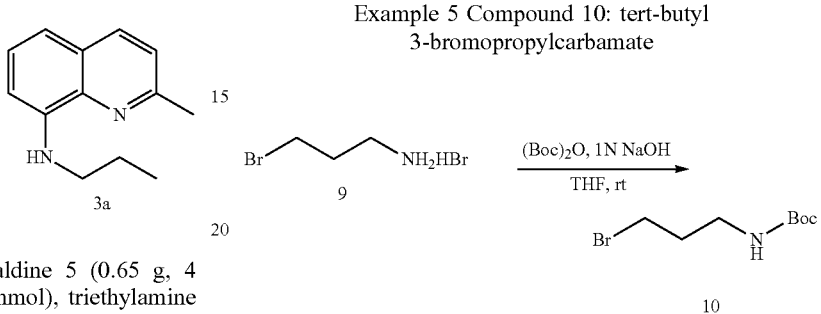

A solution of NaOH (1N, 132 mL) was added slowly to a stirred mixture of 3-bromo-propylamine hydrobromide 9 (13.40 g, 60 mmol) and Di-tert-butyl dicarbonate ($(Boc)_2O$, 13.1 g, 60 mmol) in THF (200 mL), the reaction mixture was stirred for 3 h at room temperature. After removal of the THF, the residue was redissolved in diethylether (60 mL), washed by HCl (1 N), saturated $NaHCO_3$ and NaCl, dried by $Na_2SO_4$. The mixture was filtered and concentrated to afford a pale yellow oil of compound 10 (13.42 g, 94%). $^1H$ NMR (400 MHz, $CDCl_3$): δ 3.44 (t, J=6.5 Hz, 2H), 3.29-3.25 (m, 2H), 2.08-2.01 (m, 2H), 1.44 (s, 9H).

Example 6 Compound 11: tert-butyl 3-bromopropyl(methyl)carbamate

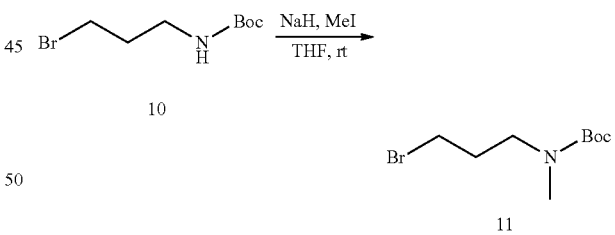

To a stirred solution of compound 10 (0.43 g, 1.8 mmol) in 8 ml anhydrous THF, was added sodium hydride (0.144 g, 3.6 mmol) in portions. The reaction mixture was stirred for 24 h, a solution of saturated $NH_4Cl$ (2 mL) was added to quench the reaction. After removal of the THF, the residue was redissolved in 15 mL diethylether, washed by saturated $NH_4Cl$ and NaCl, dried by $Na_2SO_4$, concentrated and purified by column chromatography to afford a pale yellow oil of 11 (0.385 g, 85%). $^1H$ NMR (400 MHz, $CDCl_3$): δ 3.38 (t, J=6.6 Hz, 1H), 3.33 (t, J=6.7 Hz, 1H), 3.28 (t, J=6.7 Hz, 1H), 3.13 (t, J=7.0 Hz, 1H), 2.06-2.04 (m, 2H), 1.44 (s, 9H); $^{13}C$ NMR (100 MHz, $CDCl_3$): δ 155.7, 79.5, 49.3, 47.3, 31.9, 28.4, 2.6 ppm.

Example 7 Compound 12: tert-butyl 3-(2-methylquinolin-8-ylamino)propylcarbamate

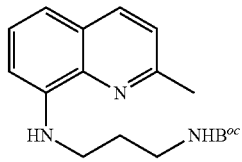 [SMILES: Cc1ccc2cccc(NCCCNC(=O)OC(C)(C)C)c2n1]

This compound was synthesized with similar procedures to that of example 3. $^1$H NMR (400 MHz, CDCl$_3$): δ 7.90 (d, J=8.4 Hz, 1H), 7.31 (dd, 7.9 Hz, 1H), 7.19 (d, J=8.4 Hz, 1H), 7.00 (d, J=8.0, Hz, 1H), 6.63 (d, J=7.5, Hz, 1H), 6.21 (s, 1H), 4.92 (s, 1H), 3.33-3.28 (m, 4H), 2.70 (s, 3H), 1.94-1.91 (m, 2H), 1.48 (s, 9H); $^{13}$C NMR (100 MHz, MeOD): δ 156.1 (C), 155.5 (C), 144.1 (C), 137.4 (C), 136.0 (CH), 126.6 (CH), 126.5 (CH), 122.0 (CH), 113.7 (CH), 104.6 (CH), 79.0 (C), 40.9 (CH$_2$), 38.6 (CH$_2$), 29.6 (CH$_2$), 28.4 (CH$_3$), 25.0 (CH$_3$) ppm. LCMS (ESI, relative intensity): m/z 316 ([M+H]$^+$, 100).

Example 8 Compound 13: tert-butyl methyl(3-(2-methylquinolin-8-ylamino)propyl)carbamate

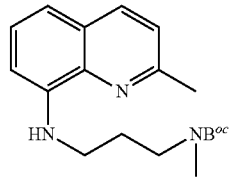 [SMILES: Cc1ccc2cccc(NCCCN(C)C(=O)OC(C)(C)C)c2n1]

This compound was synthesized with similar procedures to that of example 3. $^1$H NMR (400 MHz, CDCl$_3$): δ 7.93 (d, J=8.4 Hz, 1H), 7.30 (dd, 7.9 Hz, 1H), 7.24-7.22 (m, 1H), 7.01-6.99 (m, 1H), 6.63 (d, J=7.5, Hz, 1H), 6.18 (s, 1H), 4.92 (s, 1H), 3.42-3.39 (m, 2H), 3.33-3.32 (m, 2H), 2.90 (s, 3H), 2.69 (s, 3H), 2.05-1.98 (m, 2H), 1.47 (s, 9H); LCMS (ESI, relative intensity): m/z 330 ([M+H]$^+$, 100).

Example 9 Compound 14: 9-(diethylamino)-3-methyl-5-(propylamino)pyrido[3,2-a]phenothiazin-7-ium chloride

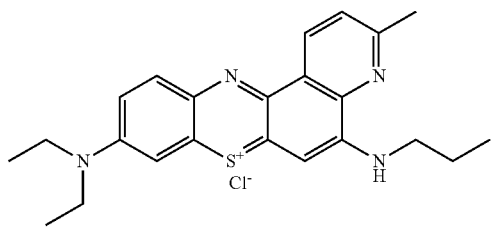 [SMILES: CCCNc1cc2[s+]c3cc(N(CC)CC)ccc3nc2c2ccc(C)nc12 ; [Cl-]]

This compound was synthesized with similar procedures to that of example 2. $^1$H NMR (400 MHz, MeOD): δ 8.77 (d, J=8.4 Hz, 1H), 7.76 (d, J=9.5 Hz, 1H), 7.61 (d, J=8.5 Hz, 1H), 7.31 (dd, J=9.5, 2.7 Hz, 1H), 7.22 (s, 1H), 7.14 (d, J=2.7 Hz, 1H), 3.67 (q, J=7.1 Hz, 4H), 3.56 (t, J=7.3 Hz, 2H), 2.71 (s, 3H), 1.86-1.80 (m, 2H), 1.34 (t, J=7.1 Hz, 6H), 1.11 (t, J=7.3 Hz, 3H); $^{13}$C NMR (100 MHz, MeOD): δ 162.0 (C), 152.9 (C), 152.8 (C), 140.8 (C), 139.8 (C), 138.5 (CH), 134.3 (C), 134.2 (CH), 133.7 (C), 133.6 (C), 128.0 (C), 127.5 (CH), 119.1 (CH), 106.4 (CH), 103.4 (CH), 47.1 (CH$_2$), 46.4 (CH$_2$), 24.9 (CH$_3$), 23.5 (CH$_2$), 13.2 (CH$_3$), 11.7 (CH$_3$) ppm. LCMS (ESI, relative intensity): m/z 391 ([M-Cl]$^+$, 100). UV-Vis (EtOH): λmax (nm) 666, log ε 5.01.

Example 10 Compound 15: 9-(diethylamino)-3-methyl-5-(pentylamino)pyrido[3,2-a]phenothiazin-7-ium chloride

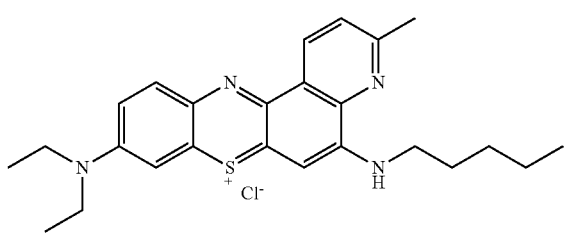

This compound was synthesized with similar procedures to that of example 2. $^1$H NMR (400 MHz, MeOD): δ 8.59 (d, J=8.4 Hz, 1H), 7.63 (d, 8.4 Hz, 1H), 7.50 (d, J=8.4 Hz, 1H), 7.24 (dd, J=9.0, 2.3 Hz, 1H), 7.05 (s, 1H), 7.03 (d, J=2.2 Hz, 1H), 3.63 (q, J=6.9 Hz, 4H), 3.50 (t, J=7.3 Hz, 2H), 2.64 (s, 3H), 1.77 (br, 2H), 1.47-1.45 (m, 4H), 1.32 (t, J=7.0 Hz, 6H), 1.00 (t, J=6.7 Hz, 3H); $^{13}$C NMR (100 MHz, MeOD): δ 161.9 (C), 152.8 (C), 152.6 (C), 140.6 (C), 139.7 (C), 138.4 (CH), 134.1 (C), 133.9 (CH), 133.5 (C), 133.4 (C), 127.7 (C), 127.4 (CH), 119.0 (CH), 106.3 (CH), 103.1 (CH), 47.0 (CH$_2$), 44.8 (CH$_2$), 30.3 (CH$_3$), 29.9 (CH$_2$), 25.0 (CH$_3$), 23.6 (CH$_2$), 14.5 (CH$_3$), 13.2 (CH$_3$) ppm. LCMS (ESI, relative intensity): m/z 419 ([M-Cl]$^+$, 100). UV-Vis (EtOH): λmax (nm) 651, log ε 4.91.

Example 11 Compound 16: 9-(diethylamino)-5-(heptylamino)-3-methylpyrido[3,2-a]phenothiazin-7-ium chloride

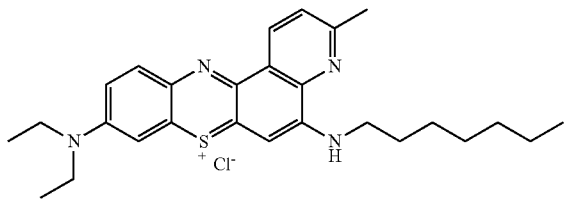

This compound was synthesized with similar procedures to that of example 2. $^1$H NMR (400 MHz, MeOD): δ 8.67 (d, J=8.1 Hz, 1H), 7.68 (d, J=9.4 Hz, 1H), 7.55 (d, J=8.2 Hz, 1H), 7.27 (d, J=9.2 Hz, 1H), 7.12 (s, 1H), 7.09 (s, 1H), 3.65 (q, J=6.9 Hz, 4H), 3.53 (t, J=6.7 Hz, 2H), 2.67 (s, 3H), 1.77 (t, J=6.4 Hz, 2H), 1.47-1.31 (m, 14H), 0.93 (t, J=6.5 Hz, 3H); $^{13}$C NMR (100 MHz, MeOD): δ 161.9 (C), 152.8 (C), 152.4 (C), 140.6 (C), 139.5 (C), 138.5 (CH), 134.2 (C), 134.1 (CH), 133.6 (C), 133.4 (C), 127.8 (C), 127.5 (CH), 119.1 (CH), 106.5 (CH), 103.3 (CH), 47.1 (CH$_2$), 44.9 (CH$_2$), 33.0 (CH$_2$), 30.2 (2CH$_2$), 28.1 (CH$_2$), 24.9 (CH$_3$), 23.7 (CH$_2$), 14.5 (CH$_3$), 13.2 (CH$_3$) ppm. LCMS (ESI, relative intensity): m/z 447 ([M-Cl]$^+$, 100). UV-Vis (EtOH): λmax (nm) 651, log ε 4.89.

Example 12 Compound 17: 5-(decylamino)-9-(diethylamino)-3-methylpyrido[3,2-a]phenothiazin-7-ium chloride

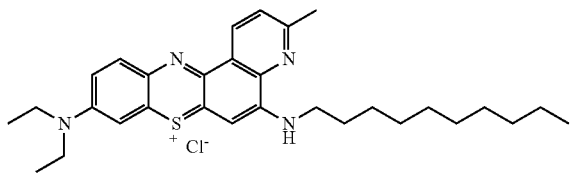

This compound was synthesized with similar procedures to that of example 2. $^1$H NMR (400 MHz, MeOD): δ 8.73 (d, J=8.4 Hz, 1H), 7.73 (d, J=9.5 Hz, 1H), 7.58 (d, J=8.4 Hz, 1H), 7.29 (dd, J=9.2, 2.8 Hz, 1H), 7.17 (s, 1H), 7.11 (d, J=2.8 Hz, 1H), 3.66 (q, J=7.1 Hz, 4H), 3.56 (t, J=7.4 Hz, 2H), 2.69 (s, 3H), 1.82-1.75 (m, 2H), 1.52-1.28 (m, 20H), 0.88 (t, J=6.7 Hz, 3H); $^{13}$C NMR (100 MHz, MeOD): δ 162.0 (C), 152.9 (C), 152.7 (C), 140.8 (C), 139.8 (C), 138.5 (CH), 134.2 (C), 134.1 (CH), 133.6 (C), 133.6 (C), 127.9 (C), 127.5 (CH), 119.1 (CH), 106.4 (CH), 103.3 (CH), 47.0 (CH$_2$), 44.8 (CH$_2$), 33.1 (CH$_2$), 30.8 (CH$_2$), 30.7 (CH$_2$), 30.5 (CH$_2$), 30.5 (CH$_2$), 30.2 (CH$_2$), 28.1 (CH$_2$), 25.0 (CH$_3$), 23.7 (CH$_2$), 14.4 (CH$_3$), 13.2 (CH$_3$) ppm. LCMS (ESI, relative intensity): m/z 489 ([M-Cl]$^+$, 100). UV-Vis (EtOH): λmax (nm) 651, log ε 4.89.

Example 13 Compound 18: 9-(diethylamino)-3-methyl-5-(methylamino)pyrido[3,2-a]phenothiazin-7-ium chloride

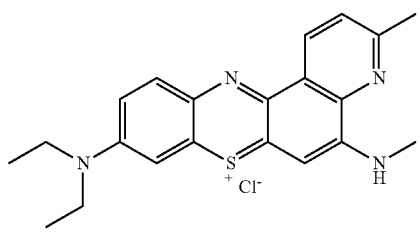

This compound was synthesized with similar procedure to that of example 2. $^1$H NMR (400 MHz, MeOD): δ 8.37 (d, J=8.3 Hz, 1H), 7.46 (d, J=9.4 Hz, 1H), 7.40 (d, J=8.3 Hz, 1H), 7.16 (dd, J=9.4, 2.2 Hz, 1H), 6.93 (d, J=2.2 Hz, 1H), 6.78 (s, 1H), 3.61 (q, J=6.9 Hz, 4H), 3.05 (s, 3H), 2.58 (s, 3H), 1.31 (t, J=7.0 Hz, 6H); $^{13}$C NMR (100 MHz, MeOD): δ 161.6 (C), 152.8 (C), 152.6 (C), 139.7 (C), 139.2 (C), 138.2 (CH), 133.5 (C), 133.4 (CH), 133.0 (C), 132.7 (C), 127.1 (CH), 126.9 (C), 118.8 (CH), 106.1 (CH), 102.7 (CH), 47.0 (CH$_2$), 30.6 (CH$_3$), 24.9 (CH$_3$), 13.3 (CH$_3$) ppm. LCMS (ESI, relative intensity): m/z 363 ([M-Cl]$^+$, 100). UV-Vis (EtOH): λmax (nm) 649, log ε 4.70.

Example 14 Compound 19: 9-(diethylamino)-5-(dipropylamino)-3-methylpyrido[3,2-a]phenothiazin-7-ium chloride

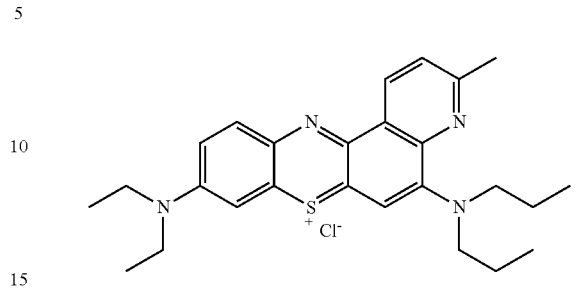

This compound was synthesized with similar procedure to that of example 2. $^1$H NMR (400 MHz, MeOD): δ 9.09 (d, J=8.5 Hz, 1H), 7.91 (d, 9.5 Hz, 1H), 7.64 (d, J=8.5 Hz, 1H), 7.37 (dd, J=9.5, 2.7 Hz, 1H), 7.32 (s, 1H), 7.21 (d, J=2.7 Hz, 1H), 4.03 (br, 4H), 3.70 (q, J=7.1 Hz, 4H), 2.69 (s, 3H), 2.00-1.90 (m, 4H), 1.34 (t, J=7.1 Hz, 6H), 1.11 (t, J=7.3 Hz, 6H); $^{13}$C NMR (100 MHz, MeOD): δ 160.3 (C), 153.9 (C), 153.0 (C), 142.8 (C), 138.6 (CH), 134.7 (C), 134.5 (CH), 134.3 (C), 133.7 (C), 130.4 (C), 126.3 (C), 126.3 (CH), 118.8 (CH), 108.8 (CH), 106.4 (CH), 58.7 (CH$_2$), 46.9 (CH$_2$), 30.7 (CH$_3$), 25.1 (CH$_3$), 22.6 (CH$_2$), 13.1 (CH$_3$), 11.4 (CH$_3$) ppm. LCMS (ESI, relative intensity): m/z 433 ([M-Cl]$^+$, 100). UV-Vis (EtOH): λmax (nm) 675, log ε 4.67.

Example 15 Compound 20: 9-(diethylamino)-5-(dipentylamino)-3-methylpyrido[3,2-a]phenothiazin-7-ium chloride

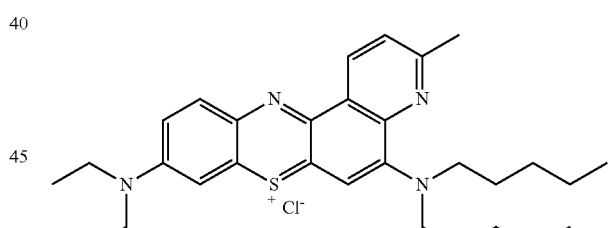

This compound was synthesized with similar procedure to that of example 2. $^1$H NMR (400 MHz, MeOD): δ 9.05 (d, J=8.4 Hz, 1H), 7.90 (d, J=9.5 Hz, 1H), 7.62 (d, J=8.5 Hz, 1H), 7.37 (dd, J=9.6, 2.8 Hz, 1H), 7.25 (s, 1H), 7.22 (d, J=2.7 Hz, 1H), 4.02 (br, 4H), 3.72-3.70 (m, 4H), 2.67 (s, 3H), 1.91 (br, 4H), 1.49-1.47 (m, 8H), 1.34 (t, J=7.1 Hz, 6H), 1.01 (t, J=6.8 Hz, 6H); $^{13}$C NMR (100 MHz, MeOD): δ 160.2 (C), 153.7 (C), 153.0 (C), 142.7 (C), 138.6 (CH), 138.4 (C), 134.7 (C), 134.4 (CH), 134.3 (C), 133.7 (C), 130.4 (C), 126.3 (CH), 118.8 (CH), 108.8 (CH), 106.5 (CH), 57.2 (CH$_2$), 46.9 (CH$_2$), 30.1 (CH$_2$), 29.0 (CH$_2$), 25.1 (CH$_3$), 23.7 (CH$_2$), 14.5 (CH$_3$), 14.4 (CH$_3$), 13.1 (CH$_3$) ppm. LCMS (ESI, relative intensity): m/z 489 ([M-Cl]$^+$, 100). UV-Vis (EtOH): λmax (nm) 676, log ε 4.89.

Example 16 Compound 21: 5-(3-aminopropylamino)-9-(diethylamino)-3-methylpyrido[3,2-a]phenothiazin-7-ium chloride

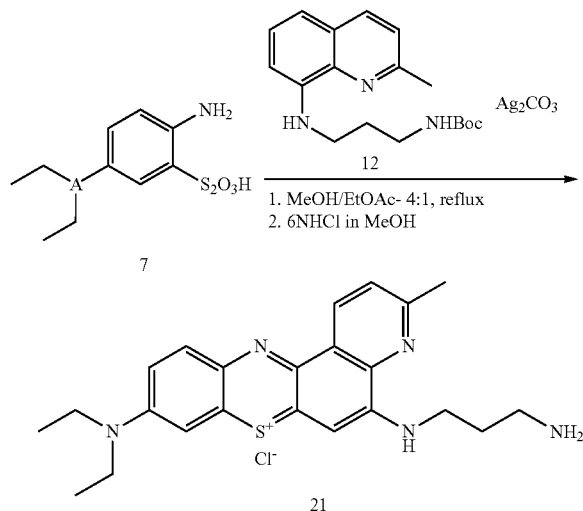

Compound 7 (0.18 g, 0.5 mmol) and compound 12 (0.1 g, 0.32 mmol) were dissolved in methanol and ethyl acetate (8 mL, MeOH/Ethyl Acetate 4:1), the mixture was stirred and heated to 80° C. Silver carbonate (0.18 g, 0.64 mmol) was added slowly, and then reflux for 2 h, a deep blue solution was obtained. After cooling to room temperature, the reaction mixture was filtered by celite, and the solid was washed by MeOH and dichloromethane. The filtrate was concentrated to leave a residue, which was purified by flash chromatography to afford a deep blue solid. The solid was redissolved in 8 mL dichloromethane, 0.2 mL HCl (6 N in MeOH) was added to the solution. The reaction mixture was stirred for 5 h at 50° C. After removal of the solvent, the residue was dried under vacuum and afford a blue solid 21 (55.2 mg, 39%). $^1$H NMR (400 MHz, MeOD): δ 8.92 (d, J=8.4 Hz, 1H), 7.89 (d, 9.6 Hz, 1H), 7.67 (d, J=8.5 Hz, 1H), 7.39 (d, J=2.6 Hz, 1H), 7.37 (s, 1H), 7.20 (d, J=2.6 Hz, 1H), 3.77 (t, J=7.2 Hz, 2H), 3.69 (q, J=10.3 Hz, 4H), 3.15 (t, J=7.4 Hz, 2H), 2.73 (s, 3H), 2.23-2.16 (m, 2H), 1.34 (t, J=7.0 Hz, 6H); $^{13}$C NMR (100 MHz, MeOD): δ 162.1 (C), 153.2 (C), 152.9 (C), 140.8 (C), 140.0 (C), 138.8 (CH), 134.9 (C), 134.2 (CH), 134.1 (C), 133.8 (C), 128.1 (C), 127.6 (CH), 119.6 (CH), 106.4 (CH), 103.1 (CH), 47.1 (CH$_2$), 41.5 (CH$_2$), 38.3 (CH$_2$), 28.0 (CH$_2$), 24.9 (CH$_3$), 13.1 (CH$_3$) ppm. LCMS (ESI, relative intensity): m/z 406 ([M-Cl]$^+$, 100). UV-Vis (EtOH): λmax (nm) 668, log ε 4.82

Example 17 Compound 22: 9-(diethylamino)-3-methyl-5-(3-(methylamino)propylamino) pyrido[3,2-a]phenothiazin-7-ium chloride

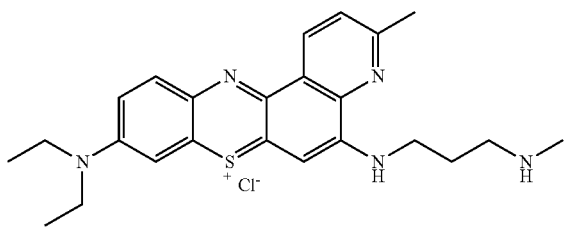

This compound was synthesized with similar procedure to that of example 14. $^1$H NMR (400 MHz, MeOD): δ 8.57 (d, J=8.3 Hz, 1H), 7.65 (d, 9.4 Hz, 1H), 7.52 (d, J=8.3 Hz, 1H), 7.31 (s, 1H), 7.29 (d, J=9.4, Hz, 1H), 7.10 (d, J=1.0 Hz, 1H), 3.76 (t, J=7.4 Hz, 2H), 3.66 (q, J=6.8 Hz, 4H), 3.25 (t, J=7.2 Hz, 2H), 2.80 (s, 3H), 2.60 (s, 3H), 2.29-2.22 (m, 2H), 1.33 (t, J=7.1 Hz, 6H); $^{13}$C NMR (100 MHz, MeOD): δ 161.7 (C), 153.0 (C), 152.2 (C), 140.2 (C), 139.3 (C), 138.7 (CH), 134.5 (C), 134.0 (CH), 133.9 (C), 133.1 (C), 127.7 (C), 127.5 (CH), 119.7 (CH), 106.5 (CH), 103.4 (CH), 47.9 (CH$_2$), 47.2 (CH$_2$), 41.9 (CH$_2$), 33.8 (CH$_3$), 26.9 (CH$_2$), 24.9 (CH$_3$), 13.3 (CH$_3$) ppm. LCMS (ESI, relative intensity): m/z 420 ([M-Cl]$^+$, 100). UV-Vis (EtOH): λmax (nm) 658, log ε 4.81.

Example 18 Compound 23: 9-(diethylamino)-6-iodo-3-methyl-5-(propylamino)pyrido[3,2-a]phenothiazin-7-ium chloride

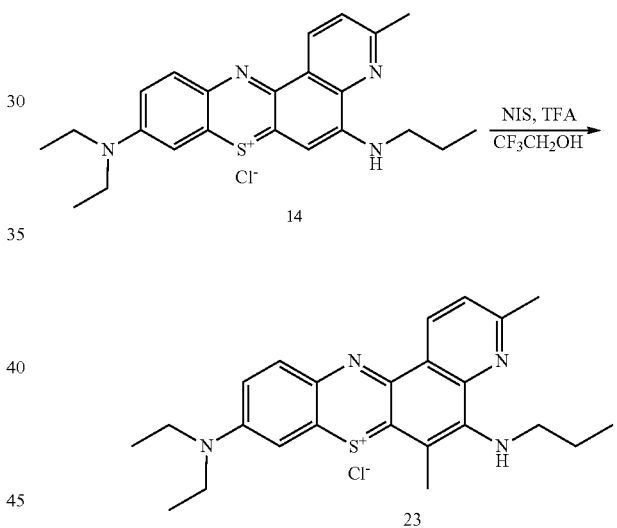

To a stirred solution of compound 14 (21 mg, 0.05 mmol) and TFA (4.2 uL, 0.055 mmol) in trifluoroethanol (6 mL), NIS (22.5 mg, 0.1 mmol) was added in portions. The reaction mixture was stirred at room temperature for 5 h, then removal of the solvent and purified by flash chromatography to afford a blue solid 23 (11.3 mg, 41%). $^1$H NMR (400 MHz, MeOD): δ 8.71 (d, J=8.4 Hz, 1H), 7.76 (d, 9.2 Hz, 1H), 7.61 (d, J=8.4 Hz, 1H), 7.41 (s, 1H), 7.13 (d, J=9.3 Hz, 1H), 3.69-3.65 (m, 4H), 3.52 (t, J=7.1 Hz, 2H), 2.75 (s, 3H), 1.91-1.84 (m, 2H), 1.36 (t, J=7.2 Hz, 6H), 1.15 (t, J=7.3 Hz, 3H); $^{13}$C NMR (100 MHz, CDCl$_3$): δ 162.1 (C), 153.8 (C), 153.4 (C), 143.7 (C), 140.1 (C), 139.2 (CH), 136.8 (C), 135.1 (C), 134.7 (C), 134.4 (CH), 128.0 (CH), 127.0 (C), 115.6 (CH), 104.2 (CH), 82.3 (C), 46.7 (CH$_2$), 40.0 (CH$_2$), 25.1 (CH$_3$), 23.7 (CH$_2$), 14.8 (CH$_3$), 11.8 (CH$_3$) ppm. LCMS (ESI, relative intensity): m/z 489 ([M-Cl—C$_2$H$_4$]$^+$, 100). UV-Vis (EtOH): λmax (nm) 633, log ε 4.87.

Example 19 Compound 24: 9-(dibutylamino)-3-methyl-5-(propylamino)pyrido[3,2-a]phenothiazin-7-ium chloride

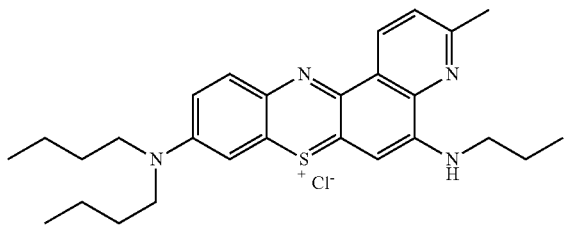

This compound was synthesized with similar procedure to that of example 2. $^1$H NMR (400 MHz, MeOD): δ 8.81 (d, J=8.4 Hz, 1H), 7.81 (d, 9.4 Hz, 1H), 7.62 (d, J=8.4 Hz, 1H), 7.30 (d, J=9.7 Hz, 1H), 7.25 (s, 1H), 7.12 (s, 1H), 3.61-3.55 (m, 6H), 2.70 (s, 3H), 1.83 (q, J=7.3 Hz, 2H), 1.76-1.68 (m, 4H), 1.54-1.45 (m, 4H), 1.10 (t, J=7.3 Hz, 3H), 1.05 (t, J=7.2 Hz, 6H); $^{13}$C NMR (100 MHz, MeOD): δ 162.0 (C), 153.3 (C), 152.9 (C), 140.9 (C), 139.9 (C), 138.5 (CH), 134.3 (C), 134.2 (CH), 133.8 (C), 133.6 (C), 128.0 (C), 127.6 (CH), 119.2 (CH), 106.5 (CH), 103.4 (CH), 52.7 (CH$_2$), 46.4 (CH$_2$), 30.9 (CH$_2$), 24.9 (CH$_3$), 23.5 (CH$_2$), 21.1 (CH$_2$), 14.3 (CH$_3$), 11.7 (CH$_3$) ppm. LCMS (ESI, relative intensity): m/z 447 ([M-Cl]$^+$, 100). UV-Vis (EtOH): λmax (nm) 654, log ε 4.86.

Example 20 Physiochemical Properties of Phenothiazine-Pyridine Compounds

All of the new prepared phenothiazine-pyridine compounds are deep blue solid, the basic physiochemical properties are measured by UV-Visible and fluorescence spectrometry. As showed in table 1, all of the compounds have strong absorption in the range of 600-700 nm, which belongs to the therapeutic window of 600-900 nm. The maximum absorption is about 650 nm in ethanol, and they are varied based on the compound structure. The fluorescence emission is about 680 nm when excited at 610 nm. All of these compounds have relatively high quantum yield, they are promising diagnostic and imaging agents. The lipophilicity is determined by the partition coefficient (log P), which can be obtained by measuring the UV-Vis absorption of the compound in phosphate buffer saline (PBS) before and after the partition equilibrium between n-octanol and PBS solution, and then calculated following the equation of: Log p=Log [(A$_{before}$/A$_{after}$)−1]. Wherein A$_{before}$ and A$_{after}$ are the absorption values in PBS solution before and after partition. All of the data are summarized in Table 1.

Example 21 Biological Activities

Cell lines and culture conditions: A549, HT29, MCF-7, MDA-MB-231 cell lines were maintained in RPMI1640 supplemented with fetal bovine serum (10%) and penicillin-streptomycin solution (1%), and WI38 cells were maintained in DMEM supplemented with fetal bovine serum (10%) and penicillin-streptomycin solution (1%). Approximately 1×10$^4$ (for A549, HT29, MCF-7, MDA-MB-231) or 1.5×10$^4$ (for WI38) cells per well were seeded in 96-well plate and incubated overnight light at 37° C. in a humidified atmosphere with 5% CO$_2$.

Dark toxicity: Cells were incubated with different concentrations of photosensitive drug for 24 h in dark, and the cell viabilities were determined by MTT assay Photocytotoxicity: Cells were incubated with different concentrations of photosensitive drug for 1 h in the dark, then the medium in the well was sucked by a syringe, and washed by PBS. Then a solution of new medium was added, and illuminated by light. After irradiation, the cells were incubated under dark at 37° C. for another 24 h, and the cell viabilities were determined by MTT assay.

The IC$_{50}$ values (50% inhibitory concentration) of the prepared phenothiazine-pyridine compounds 8, 14, 15, 16, 17, 18, 19, 20, 21, 22, 23, and 24 to normal fibroblast cell line WI38 were measured by MTT assay. The results were showed in Table 2.

Table 3 showed the photocytotoxicity and dark toxicity of the prepared phenothiazine-pyridine compounds against various tumor cell lines (A549, HT29 and MCF-7 cell lines) by MTT assay.

As shown in Table 2, the IC$_{50}$ values for most of the phenothiazine-pyridine compounds to WI38 cells are higher than 10 uM, which indicates they may have low toxicities to normal tissues. Also we can see from Table 3, these compounds showed good photoactivities to the tested tumor cell lines, and they are much more active than methylene blue against HT29 cells under the same condition and that of some literatures reported results. In addition, this type of compound showed good selectivity among different tumor cells. Especially for compound 14, it showed strong photocytotoxicity while low dark toxicity. This therapeutic advantage of excellent selectivity and activity has a great significance in clinical application. FIG. 1 shows the cytotoxic effects of compound 8, 14, 24, and 23 in the absence (closed symbols) and presence (open symbols) of light (635 nm Laser) against MDA-MB-231 cells.

Figure 2:
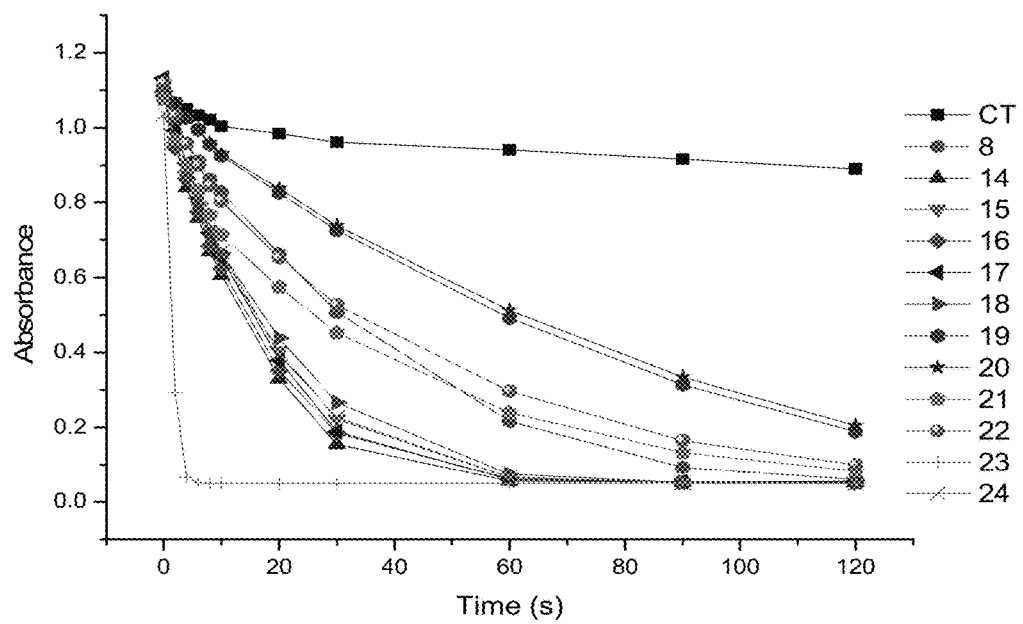
FIG. 2 shows the $^1O_2$ generation efficiency of the prepared compounds (all at 2 uM) by monitoring the decay rate of 1,3-diphenylisobenzofuran (DPBF) under light irradiation (630 LED light) in EtOH.

Example 22 the Photosensitive Efficiency of Phenothiazine-Pyridine Compounds The mechanism of using photosensitizer for PDT is predominately through the generation of reactive oxygen species (ROS) to directly or indirectly destroy the cells or tissues, and singlet oxygen is recognized as the major cytotoxic species. The singlet oxygen generation efficiency through photosensitization is an important indicator for evaluating a photosensitizer. We employed a conventional steady-state method using 1,3-diphenylisobenzofuran (DPBF) as the scavenger, which reacts irreversibly with singlet oxygen to cause the decay of DPBF. The concentrations of DPBF in EtOH at various irradiation time slots are measured by UV/Vis spectrometry. The drug solution (2 uM in EtOH) was irradiated with 630 nm LED light (106 Mw/cm$^2$), and the results were showed in FIG. 2. All of these compounds are efficient singlet oxygen generators, and for some of the analogs, they could achieve a 80% photosensitive efficiency only under irradiation for 30 s (3.2 J/cm$^2$, photosensitization efficiency=the reduction of OD value for the treated group/OD value for the control group). The photosensitive efficiency follows the tendency: 23>>14>16>17>15≈24>18>21>8>22>19≈20. Compound 23 shows the highest efficiency for the introduction of heavy atom of iodine, which enhances the intersystem crossing ability and thus increases the generation efficiency of singlet oxygen.

Figure 3:
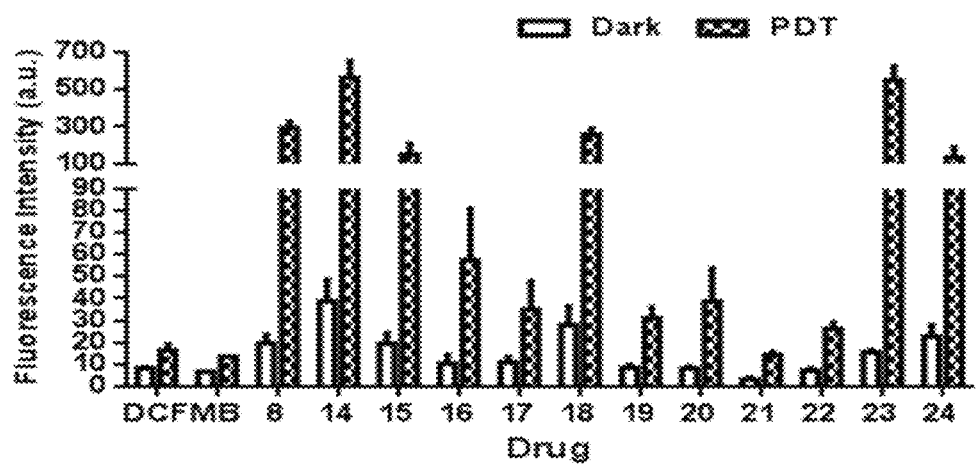
FIG. 3 shows the intracellular reactive oxygen species (ROS) generation efficiency in HT29 cells using 2,7-dichlorofluorescin diacetate (DCFH-DA) as a probe in the absence and presence of light.

In order to further mimic the biological environment, we measured the intracellular reactive oxygen species (ROS) generation efficiency of these phenothiazine-pyridine compounds by flow cytometry. We employed HT29 cell line as cell model, and 2,7-dichlorofluorescin diacetate (DCFH-DA) as the intracellular ROS indicator, to determine the fluorescence intensity of 2,7-dichlorofluorescin (DCF), which was oxidized from DCFH-DA by ROS. The experiments were repeated for three times using DCFH-DA as control. For comparison, methylene blue was used as positive control. The data were analyzed by GraphPad Prism 6, the drug concentrations are all at 0.5 uM. As shown in FIG. 3, the photosensitive efficiency of these compounds is followed by: 14≈23>8>18>15>24>>16>20>17≈19≈22>21>>MB. All of these compounds can generate ROS efficiently in cell under light irradiation with 0.5 uM concentration, while MB has almost no ROS generation under the same condition. In addition, the intracellular ROS generation efficiency is different from that measured in organic solvent, which may be attributed to the different cellular uptake amount for various compounds and the generation of some other ROS species other than $^1O_2$ in cells (Type II mechanism).

Example 23 Illumination Time Dependent Photocytotoxicities

Figure 4:
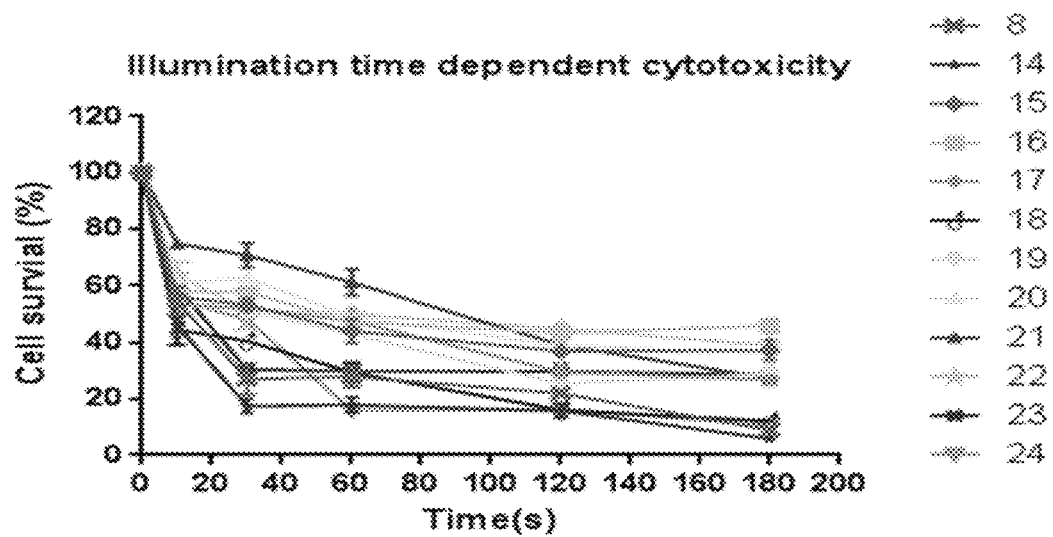
FIG. 4 shows photodynamic activity on HT29 cells under different irradiation times using 630 LED light (106 Mw/cm$^2$), all at 0.5 uM.
Figure 5:
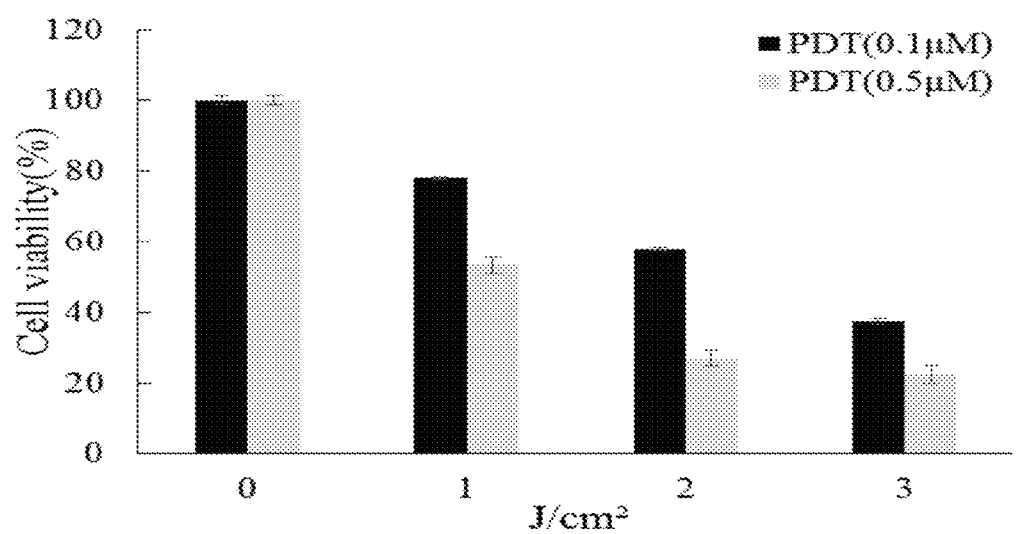
FIG. 5 shows photodynamic activity of compound 14 against MDA-MB-231 cells under different light dosages using 635 Laser.

The cells were incubated with 0.5 uM drug solution for 1 h, after removal of the medium, rinsed by PBS, new medium were added, and then were irradiated for 0, 10, 30, 60, 120, 180 s using 630 LED light. After incubation for a further 24 h, 3-(4,5-Dimethylthiazol-2-yl)-2,5-diphenyltetrazolium bromide (MTT) were added and the cells were incubated for another 4 h. The medium were sucked by syringe, and dimethyl sulfoxide (DMSO) was added to fully dissolve the crystals, the optical density (OD) values were measured with a microplate reader, and the data were analyzed by Graph-Pad Prism 6. As shown in FIG. 4, most of the compounds showed a time dependent photocytotoxicity against HT29 cells. FIG. 5 shows the light dosage dependent photocytotoxicity of compound 14 against MDA-MB-231 cells using 635 Laser.

Example 24 Photodynamic Inactivation of Bacteria

Bacterial growth and culture: Gram-positive *S. aureus* or Gram-negative *E. coli* were grown on trypticase soy agar (TSA) for 24 h, then a colony was transferred into tryptica soy broth (TSB) and grown at 37° C. overnight at a 200 rpm speeds of shaking-up using a shaker incubator. The nutrient medium was centrifuged for 5 min at 8000 rpm and diluted by sterile 0.85% saline (pH 7.5) to concentrations of $10^8$ CFU/ml, which was used for further incubation with photosensitizers in the following experiments.

Cellular uptake of photosensitizer in bacteria: Cellular uptake was performed using compound 8 as an example on *S. aureus*. Compound 8 was added into bacterial suspension to a final concentration of 0.5 uM, each sample with 1 mL was removed at the time slots of 0, 5, 10, 15, 20, 30, 45, 60, 75, 90, 105 min. All samples were rinsed twice with 0.85% saline, then using alkali lysis method that reported previously to fast pyrolysis bacteria, and to measure the fluorescence of the supernatants. The relative fluorescence intensity at various time slots represented the amount of photosensitizer taken up by bacteria.

Dark toxicities of the photosensitizers on bacteria: Bacterial suspensions were incubated with photosensitizers at various concentrations at 37° C. in the dark for 6 h. After that, 100 uL of cell suspension were spread on the TSA in 10-fold serial dilutions. Colony forming unit (CFU) was counted after incubation for 24 h at 37° C.

Photodynamic inactivation of bacteria: Bacterial suspensions ($2\times10^8$ CFU/ml) were co-incubated with different concentrations of the photosensitizer for 10 min at 37° C., and then centrifuged, washed once with normal saline and resuspended in PBS saline. Aliquots of this suspension were placed into 24-well flat bottom plate and illuminated with laser light. After illumination, 100 uL of cell suspension were spread on the TSA in 10-fold serial dilutions and colony forming unit (CFU) was counted after incubation for 24 h at 37° C.

Figure 6:
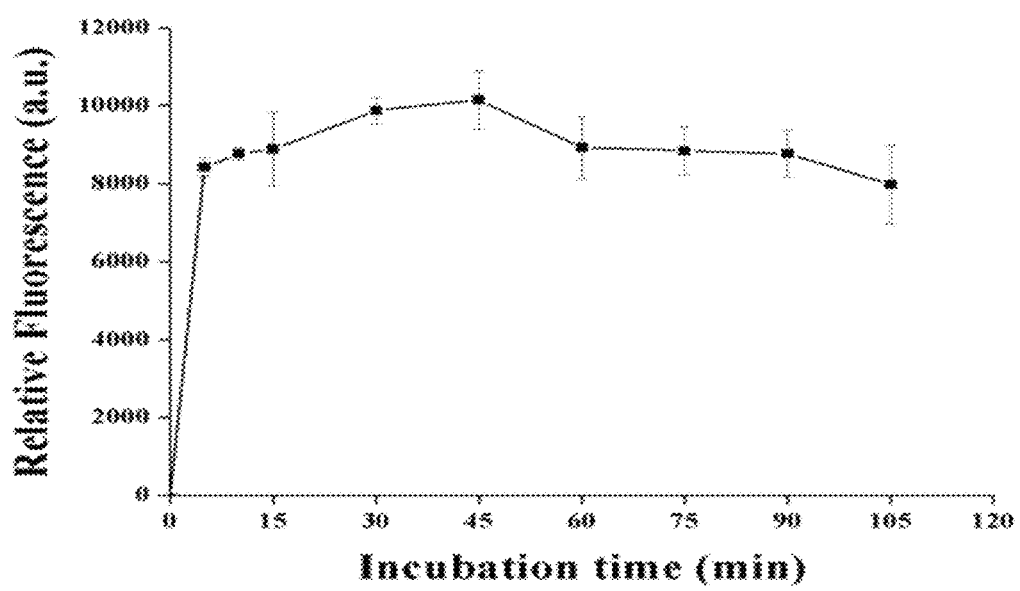
FIG. 6 shows the cellular uptake of compound 8 by *Staphylococcus aureus* (*S. aureus*).
Figure 7A:
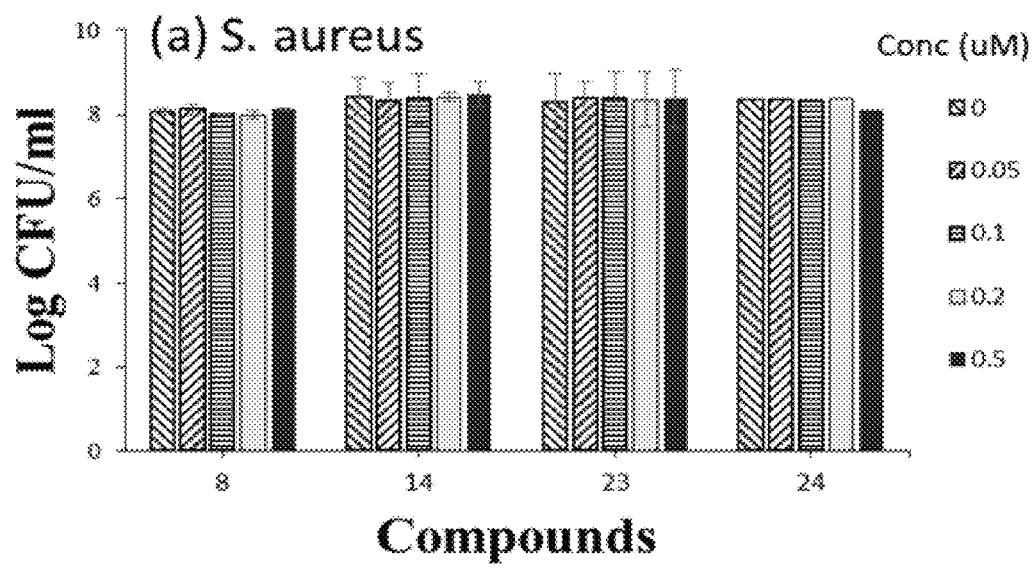
FIGS. 7A-7B show the cytotoxicity of compounds (8, 14, 23, and 24) to *S. aureus* (7A) and *Escherichia coli* (*E. coli*) (7B) in the absence of light.
Figure 7B:
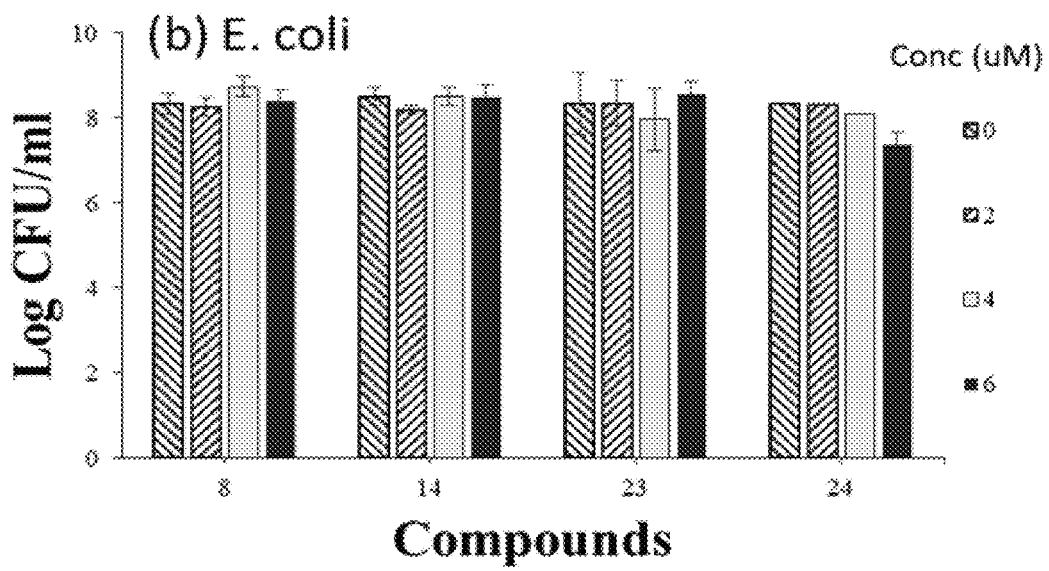
Figure 8A:
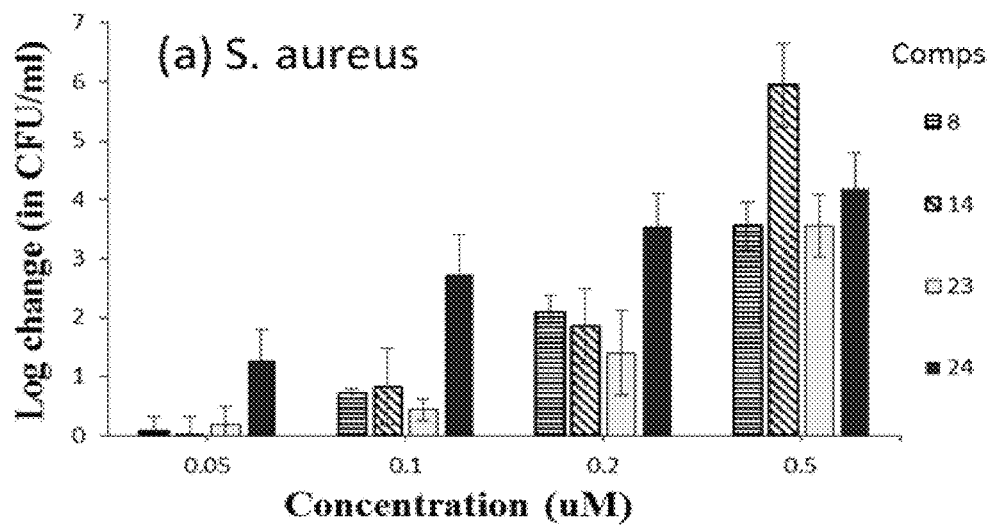
FIGS. 8A-8B show the cytotoxicity of compounds (8, 14, 23, and 24) to *S. aureus* (8A, light dose=30 J/cm$_2$) and *E. coli* (8B, light dose=50 J/cm$_2$) in the presence of light (635 Laser).
Figure 8B:
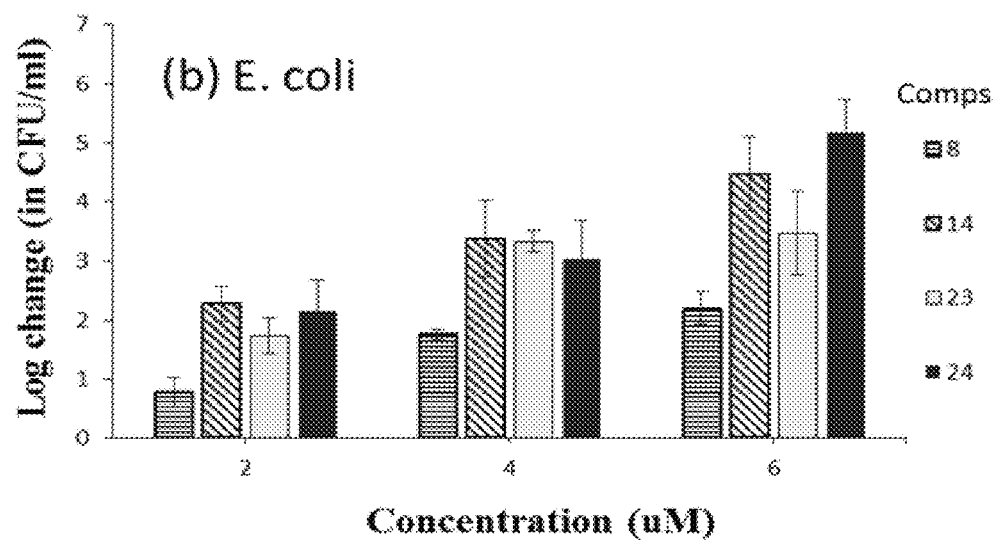
Figure 9A:
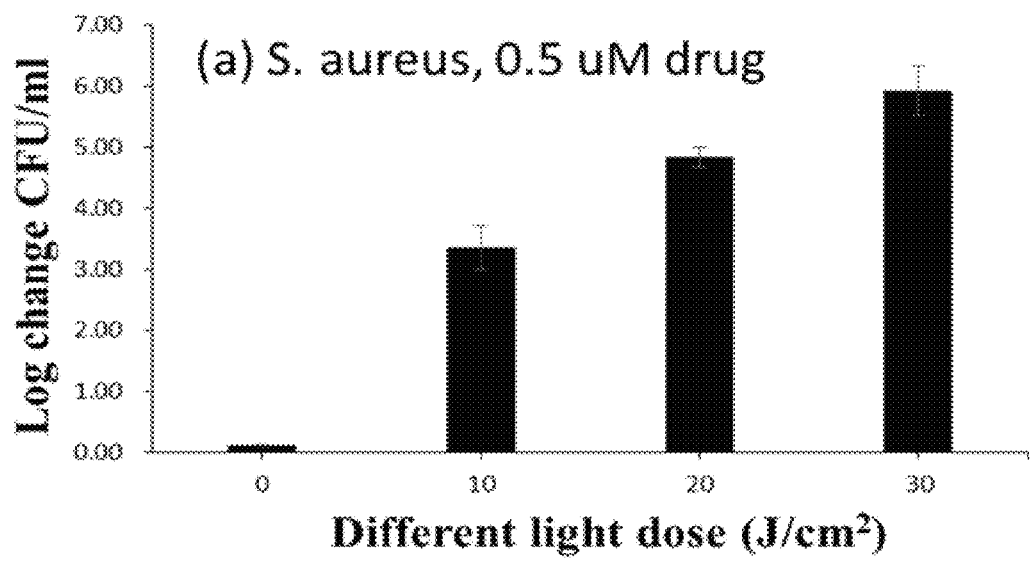
FIGS. 9A-9B show the cytotoxicity of compound 14 to *S. aureus* (9A) and *E. coli* (9B) in the 5 presence of different light dosages.
Figure 9B:
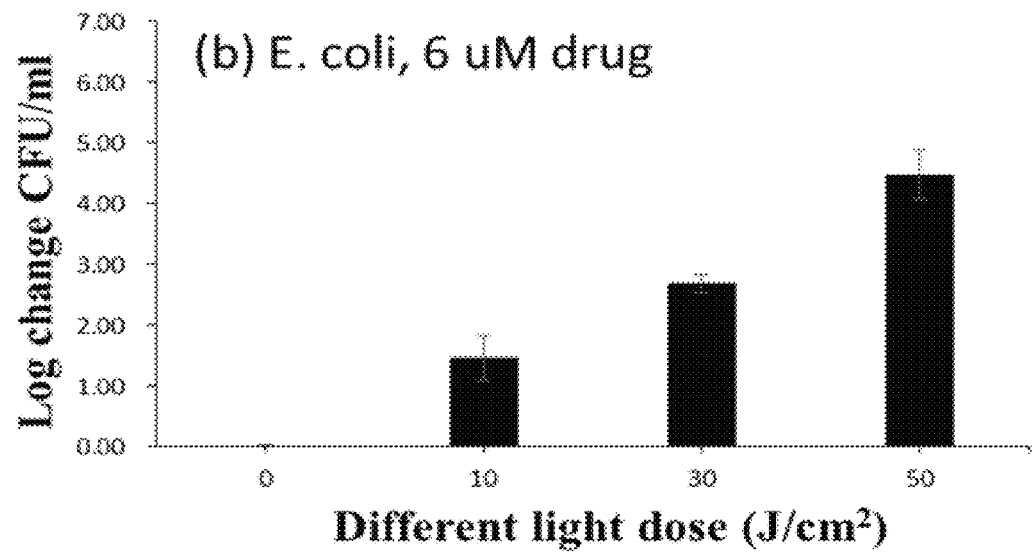

FIG. 6 shows the cellular uptake of compound 8 by *S. aureus*. It demonstrated that compound 8 could be quickly taken up by *S. aureus*, and it reached the peak at about 30 min. This short cellular uptake time has a great significance in clinical application. Not only can it lower the tendency of drug take-up by normal tissue, but also can reduce the cost of hospitals and patients. In the subsequent experiments, we choose 10 min for drug co-incubation, and to compare the antibacterial effects of different drugs. FIG. 7 shows the dark toxicity of compounds (8, 14, 23, 24) to *S. aureus* (a) and *E. coli* (b). It showed that these compounds were essentially non-toxic in the absence of light. FIG. 8 shows the photocytotoxicity of compounds 8, 14, 23 and 24 to *S. aureus* (a, light dosage=30 J/cm$^2$) and *E. coli* (b, light dosage=50 J/cm$^2$) in the presence of light. All of these compounds exhibited a concentration-dependent photocytotoxicity. An apparent killing effect to *S. aureus* occurred under concentration of 0.05 uM and 30 J/cm$^2$ of light dosage, and an apparent killing effect also occurred to *E. coli* under 2 uM concentration and 50 J/cm$^2$ of light dosage. Particularly, compound 14 could lead to about 99.9999% (6-log 10-reduction) eradication to *S. aureus* with 0.5 uM concentration and 30 J/cm$^2$ of light dosage, and about 99.999% (5-log 10-reduction) eradication to *E. coli* with 6 uM concentration and 50 J/cm$^2$ of light dosage. FIG. 9 shows the cytotoxicity of compound 14 to *S. aureus* (a, 0.5 uM drug) and *E. coli* (b, 6 uM drug) under different light dosages. It indicated that the photocytotoxicity is light dosage dependent. In clinical application, the pathogenic bacteria could be efficiently eradicated by controlling the light dosage.

The compounds presented in this invention (such as compounds 8, 14, 23, 24) could fast and efficiently eradicate pathogenic microorganisms of Gram-positive bacteria-*S. aureus* and Gram-negative bacteria-*E. coli*, under low drug concentration and light dosage. The efficient concentration and light dosage are much lower than that of literature reported compounds and some of the clinically applied photosensitizers (e.g. porphyrin-based compound and its prodrug 5-aminolevulinic acid (ALA)). (2011, 2013, 2014). What is more, the photoacitvities of these compounds also exceed that of methylene blue (clinically used) and PPA904 that developed by Stanley B. Brown (2008). As for *S. aureus*, a concentration of 10 uM PPA904 and a time of 30 min drug-incubation are required to achieve 4-log 10-reduction under 60 J/cm$^2$ of light dosage, while for *E. coli*, only 0.5-log 10-reduction could be achieved under 24 J/cm$^2$ light dosage and 30 min incubation for 10 uM of methylene blue, and only 3-log 10-reduction could be achieved for PPA904 under the same condition. However, an obvious dark toxicity occurred for both methylene blue and PPA904 under concentration of 10 uM. Therefore, the compounds presented in this invention exhibited significant value for application in photodynamic inactivation of microorganisms.

All patents, patent applications, and other publications, including GenBank Accession Numbers, cited in this application are incorporated by reference in the entirety for all purposes.

LIST OF REFERENCES

1. Wainwright M, et. al. Photobactericidal activity of phenothiazinium dyes against methicillin-resistant strains of *Staphylcoccus aureus*. *FEMS Microbiology Letters*, 1998, 160, 177-181.
2. Stanley B. Brown, et. al. In vitro photodynamic activity of a series of methylene blue analogues. *Photochemistry and photobiology*. 2002, 75, 392-397.
3. Stanley B. Brown, et. al. Biologically active methylene blue derivatives 2008, U.S. Pat. No. 7,371,744B2.
4. Gitika B. Kharkwal, et. al. Photodynamic therapy for infections: Clinical Applications. *Lasers Surg Med.* 2011, 43, 755-767.
5. Wainwright M, et. al. Phenothiazine photosensitizers. Activity of methylene blue derivatives against pigmented melanoma cell lines. *Journal of Chemotherapy.* 2012, 12, 94-104.
6. Felipe F Sperandio, et. al. Antimicrobial Photodynamic Therapy to Kill Gram-negative Bacteria. *Recent Pat Anti-infect Drug Discov.* 2013, 8, 108-120.
7. Febian Cieplik, et. al. Antimicrobial Photodynamic Therapy for inactivation of biofilms formed by oral key pathogens. *Frontiers in microbiology.* 2014, 5, 405-421.

TABLE 1

Physiochemical properties of phenothiazine-pyridine compounds

| Compound | λmax(nm) in EtOH | Log ε | λEm (nm) | LogP |
|---|---|---|---|---|
| 8 | 658 | 4.93 | 680 | 0.97 |
| 14 | 666 | 5.01 | 684 | 1.34 |

TABLE 1-continued

Physiochemical properties of phenothiazine-pyridine compounds

| Compound | λmax(nm) in EtOH | Log ε | λEm (nm) | LogP |
|---|---|---|---|---|
| 15 | 651 | 4.91 | 684 | 1.40 |
| 16 | 651 | 4.89 | 684 | 1.44 |
| 17 | 651 | 4.89 | 684 | 2.49 |
| 18 | 649 | 4.70 | 683 | 1.31 |
| 19 | 675 | 4.67 | 684 | 1.42 |
| 20 | 676 | 4.89 | 700 | 1.48 |
| 21 | 668 | 4.82 | 686 | 0.64 |
| 22 | 658 | 4.81 | 686 | 0.65 |
| 23 | 633 | 4.87 | 666 | 1.48 |
| 24 | 654 | 4.86 | 688 | 3.40 |

TABLE 2

Dark toxicity to normal fibroblast WI38 cells.

| Compounds | $IC_{50}(uM)$[1] |
|---|---|
| 8 | >10 |
| 14 | >10 |
| 15 | >10 |
| 16 | >10 |
| 17 | 7.0 |
| 18 | 5.0 |
| 19 | 9.4 |
| 20 | >10 |
| 21 | >10 |
| 22 | >10 |
| 23 | 5.2 |
| 24 | >10 |

[1] Cells were incubated under dark with the phenothiazine-pyridine compound for 24 h, and the cell viabilities were assessed by MTT assay.

TABLE 3

Photocytotoxicity and dark toxicity to different tumor cells

| | IC50 (uM) | | | | | | | | |
|---|---|---|---|---|---|---|---|---|---|
| | A549 cell line | | | MCF7 cell line | | | HT29 cell line | | |
| Comps | PDT[1] | DK[2] | Ratio of DK/PDT | PDT[1] | DK[2] | Ratio of DK/PDT | PDT[1] | DK[2] | Ratio of DK/PDT |
| 8 | 1.8 | 6.5 | 3.6 | 0.50 | 1.1 | 2.2 | 0.21 | 4.6 | 21.9 |
| 14 | 0.34 | 3.1 | 9.1 | 0.37 | 1.9 | 5.1 | 0.039 | 2.1 | 53.8 |
| 22 | 11.9 | 19.8 | 1.7 | 3.1 | 13.2 | 4.3 | 0.51 | 9.5 | 18.6 |
| 23 | 0.68 | 3.3 | 4.9 | 0.12 | 0.9 | 7.5 | 0.071 | 2.0 | 28.2 |
| 24 | 0.10 | 0.85 | 8.5 | 0.077 | 0.85 | 11.0 | 0.074 | 0.84 | 11.4 |
| MB | | | | | | | 9.2 (88.5[3]) | >10 | — |

[1] Cells were incubated with the phenothiazine-pyridine compound for 1 h, then the medium in the well was sucked by a syringe, and the cells were washed by PBS (100 uL × 1). Then a solution of new medium (100 uL) was added, and treated with a 630 nm LED light for 30 s with a density of 3.2 J/cm². After irradiation, the cells were incubated in the dark for 24 h, cell viability was assessed by MTT assay.

[2] Cells were incubated under dark with the phenothiazine-pyridine compound for 24 h, and the cell viability was assessed by MTT assay.

[3] Stanley B. Brown reported value with 664 laser and 3 J/cm² light dose (2008).

What is claimed is:

1. A phenothiazine-pyridine compound of formula (I):

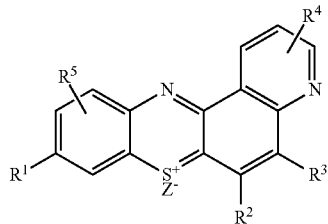

wherein:

$R^1$ and $R^3$ are each

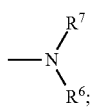

$R^2$ is H or halogen;

$R^4$ is H, halogen, —$NH_2$, —OH, —CN, —$NO_2$, —$COCH_3$, —$CF_3$, $C_1$-$C_{10}$ alkyl, $C_1$-$C_{10}$ alkoxy, $C_1$-$C_{10}$ haloalkyl, $C_3$-$C_6$ cycloalkyl,

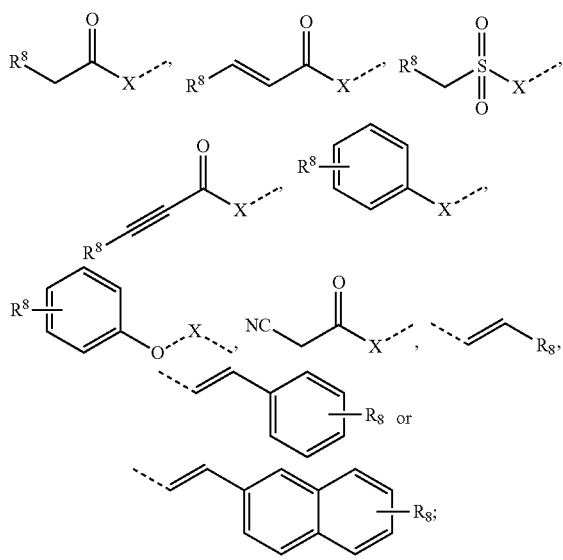

$R^5$ is H, halogen, —CN, —$NO_2$, —$COCH_3$, —$CF_3$, $C_1$-$C_{12}$ alkyl, $C_1$-$C_{12}$, alkoxy, $C_1$-$C_6$ alkoxycarbonyl, $C_3$-$C_6$ cycloalkyl or $C_2$-$C_{10}$N-alkyl amine;

$R^6$ and $R^7$ are each independently H, $C_1$-$C_{12}$ alkyl, $C_3$-$C_6$ cycloalkyl, $C_3$-$C_{12}$ alkenyl, $C_3$-$C_{12}$ alkynyl, $C_2$-$C_{10}$ amine or $C_2$-$C_{10}$ substituted amine, aryl, $C_nH_{2n}Y$, $YC_nH_{2n}Y$, or when taken together, $R^6$ and $R^7$ with a nitrogen to which they are both attached form a 5 to 7 membered heterocyclic ring wherein any one carbon atom of said heterocyclic ring can optionally be replaced with —O—, —S—, —$SO_2$— or NR—;

each $R^8$ is independently H, halogen, —$NO_2$, —CN, —$COCH_3$, —$CF_3$, $C_1$-$C_6$alkyl, $C_1$-$C_6$ alkoxy, $C_3$-$C_6$cycloalkyl or aryl;

each $R^9$ is independently H, $C_1$-$C_{10}$ alkyl, $C_2$-$C_9$ carbonyl or $C_2$-$C_9$ sulfonyl;

each n is independently an integer from 2 to 6;

each X is independently selected from $C_1$-$C_5$ alkyl, O, S, $NH_2$, NH or $NR^{10}$;

each Y is independently F, Cl, Br, I, OH, OMe, $OC_2H_5$, $OC_3H_7$, CN or $OCOCH_3$;

each $R^{10}$ is independently $C_1$-$C_6$ alkyl, $C_1$-$C_6$ alkoxy, —$NO_2$, —CN, —$COCH_3$ or aryl;

$Z^-$ is an organic or inorganic counter anion;

or salts thereof.

2. The compound according to claim 1, wherein $R^4$ is H, $C_1$-$C_{12}$ alkyl, $C_1$-$C_{10}$ alkyl, $C_1$-$C_{10}$ alkoxy or $C_3$-$C_6$ cycloalkyl.

3. The compound according to claim 1, wherein $R^4$ is H, —$CH_3$, —$C_2H_5$, —$C_3H_7$, —$OCH_3$, —$OC_2H_5$, —$OC_4H_9$, -cyclopropyl, -cyclobutyl, -cyclopentyl or cyclohexyl.

4. The compound according to claim 1, wherein $R^6$ and $R^7$ are each independently H, methyl, ethyl, propyl, n-butyl, n-pentyl, n-hexyl, n-heptyl, n-octyl, cyclopropyl, cyclobutyl, cyclopentyl, cyclohexyl, —$CH_2(CH_2)_2NH_2$, —$CH_2(CH_2)_3NH_2$, —$CH_2(CH_2)_4NH_2$, —$CH_2(CH_2)_5NH_2$, —$N(CH_3)(CH_2)_2NH_2$, $N(CH_3)(CH_2)_3NH_2$, $N(CH_3)(CH_2)_4NH_2$ or $N(CH_3)(CH_2)_5NH_2$.

5. The compound according to claim 1, wherein when taken together, $R^6$ and $R^7$ with a nitrogen to which they are both attached form a form a 5 to 7 membered heterocyclic ring wherein any one carbon atom of said heterocyclic ring can optionally be replaced with —O—, —S—, —$SO_2$— or —$NR^9$—.

6. The compound according to claim 1, wherein $R^6$ and $R^7$ are

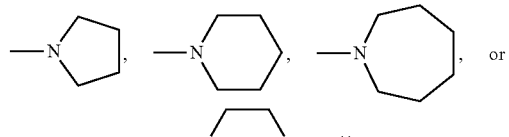

wherein $R^{11}$ is H, $C_1$-$C_{10}$ alkyl, $C_2$-$C_9$ carbonyl, or $C_2$-$C_9$ sulfonyl.

7. The compound according to claim 1, wherein $R^6$ and $R^7$ are each independently H or $C_1$-$C_{12}$ alkyl.

8. The compound according to claim 1, wherein $R^6$ and $R^7$ form a six membered azaoxa-ring or azathia-ring.

9. The compound according to claim 1, wherein $R^6$ and $R^7$ form

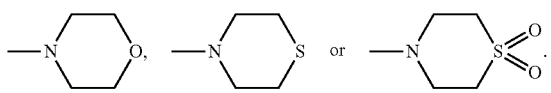

10. The compound according to claim 1, wherein $Z^-$ is a halide ion, $NO_2$—, $CH_3CO_2$—, $NO_2^-$, $CH_3CO_2^-$, $CF_3CO_2^-$, $ClO_4^-$, $HSO_4^-$, $H_2PO_4^-$, $SCN^-$, $F_4B^-$, lactate, citrate, tartrate, malate, glycolate, glycerate, gluconate, glutamate, or aspartate.

11. The compound according to claim 1, wherein $Z^-$ is $F^-$, $Cl^-$, $Br^-$, $I^-$, $CH_3COO^-$, $CF_3COO^-$ or $HSO_4^-$.

12. The compound according to claim 1, wherein the phenothiazine-pyridine has the structure of Formula II:

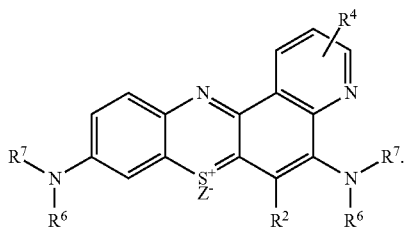

(II)

13. The compound according to claim 1, wherein the phenothiazine-pyridine has the structure of Formula III:

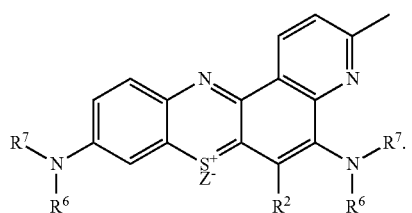

(III)

14. The compound according to claim 1, wherein the compound is 5-amino-9-(diethylamino)-3-methylpyrido[3,2-a]phenothiazin-7-ium chloride, 9-(diethylamino)-3-methyl-5-(propylamino)pyrido[3,2-a]phenothiazin-7-ium chloride, 9-(diethylamino)-3-methyl-5-(pentylamino)pyrido[3,2-a]phenothiazin-7-ium chloride, 9-(diethylamino)-5-(heptylamino)-3-methylpyrido[3,2-a]phenothiazin-7-ium chloride, 5-(decylamino)-9-(diethylamino)-3-methylpyrido[3,2-a]phenothiazin-7-ium chloride, 9-(diethylamino)-3-methyl-5-(methylamino)pyrido[3,2-a]phenothiazin-7-ium chloride, 9-(diethylamino)-5-(dipropylamino)-3-methylpyrido[3,2-a]phenothiazin-7-ium chloride, 9-(diethylamino)-5-(dipentylamino)-3-methylpyrido[3,2-a]phenothiazin-7-ium chloride, 5-(3-aminopropylamino)-9-(diethylamino)-3-methylpyrido[3,2-a]phenothiazin-7-ium chloride, 9-(diethylamino)-3-methyl-5-(3-(methylamino)propylamino)pyrido[3,2-a]phenothiazin-7-ium chloride, 9-(diethylamino)-6-iodo-3-methyl-5-(propylamino)pyrido[3,2-a]phenothiazin-7-ium chloride or 9-(dibutylamino)-3-methyl-5-(propylamino)pyrido[3,2-a]phenothiazin-7-ium chloride.

15. A pharmaceutical composition comprising the compound of claim 1 and a pharmaceutically acceptable excipient.

16. A method for inhibiting cell proliferation, comprising:
(a) contacting a target cell with an effective amount of the compound of claim 1; and
(b) exposing the compound to a light having a wavelength of about 600-900 nm, thereby causing death of the target cell.

17. The method of claim 16, wherein the target cell is a tumor cell or a bacterial cell.

18. The method of claim 16, wherein the target cell is within a subject's body.

19. The method of claim 16, wherein the light's wavelength is about 600-700 nm.

20. The method of claim 18, where the subject is a human or animal.

21. The method of claim 18, wherein the subject has a tumor.

22. The method of claim 21, wherein the tumor is lung cancer, pancreatic cancer, breast cancer, colorectal cancer, colon cancer, esophageal cancer, oral cancer, lymphoma, penis cancer, prostate cancer, skin cancer, gynecological cancer, gastrointestinal stromal tumor, head tumor, neck tumor, or eye tumor.

23. The method of claim 18, wherein the subject has a bacterial infection.

24. The method of claim 23, wherein the bacterial infection is a Gram-positive bacterial infection or a Gram-negative bacterial infection.

25. The method of claim 23, wherein the bacterial infection is *E. coli* infection or *S. aureus* infection.

26. The method of claim 18, wherein the compound is administered to the subject by oral ingestion, topical application, or injection.

27. The method of claim 26, wherein the injection is subcutaneous, intravenous, intramuscular, intraperitoneal, or intratumoral injection.

28. A composition comprising the compound of claim 1 and a proliferating cell.

29. The composition of claim 28, wherein the cell is a tumor cell or a bacterial cell.

30. The composition of claim 29, which is further being exposed to a light having a wavelength of about 600-900 nm.

\* \* \* \* \*